United States Patent [19]

Ishida et al.

[11] 4,086,417
[45] Apr. 25, 1978

[54] CYTIDINE NUCLEOTIDE DERIVATIVES

[75] Inventors: Torao Ishida; Minoru Akiyama, both of Fuji; Yoshio Sakurai, Mitaka; Shigeru Tsukagoshi, Tokyo, all of Japan

[73] Assignee: Asahi Kasei Kogyo Kabushiki Kaisha, Osaka, Japan

[21] Appl. No.: 622,794

[22] Filed: Oct. 15, 1975

[30] Foreign Application Priority Data

Oct. 15, 1974  Japan ................................ 49-117664
Nov. 27, 1974  Japan ................................ 49-135574

[51] Int. Cl.² ........................................... C07H 19/10
[52] U.S. Cl. ..................................... 536/29; 424/180; 536/23
[58] Field of Search .................. 260/211.5 R; 536/29, 536/23

[56] References Cited

U.S. PATENT DOCUMENTS

| | | | |
|---|---|---|---|
| 3,317,512 | 5/1967 | Wechter ........................ | 260/211.5 R |
| 3,423,399 | 1/1969 | Honjo et al. .................. | 260/211.5 R |
| 3,457,253 | 7/1969 | Wechter ........................ | 260/211.5 R |
| 3,773,755 | 11/1973 | Nagyvary ..................... | 536/29 |
| 3,804,827 | 4/1974 | Robins et al. ................. | 260/211.5 R |
| 3,894,000 | 7/1975 | Wechter et al. .............. | 260/211.5 R |

Primary Examiner—Johnnie R. Brown
Attorney, Agent, or Firm—Sughrue, Rothwell, Mion Zinn and Macpeak

[57] ABSTRACT

A nucleotide derivative represented by the general formula:

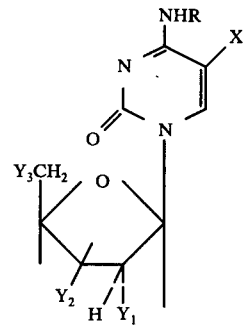

wherein R represents an acyl group having 14 – 22 carbon atoms and having an aliphatic acyl moiety; X represents a hydrogen atom, a halogen atom, an alkyl group having 1 – 4 carbon atoms, or a trifluoromethyl group; and at least one, but not all, of $Y_1$, $Y_2$, and $Y_3$ represents a phosphate, a pyrophosphate, a triphosphate, or a salt thereof, the balance of $Y_1$, $Y_2$ and $Y_3$ representing a hydroxyl group; or in case of ribosyl, $Y_1$ and $Y_3$, or $Y_2$ and $Y_3$ represent, at the same time, the aforesaid phosphate, pyrophosphate, triphosphate or salt thereof and the remaining group of $Y_1$, $Y_2$ or $Y_3$ represents a hydroxyl group; or in case of arabinosyl, $Y_1$ and $Y_2$, or $Y_2$ and $Y_3$ represent, at the same time, the aforesaid phosphate, pyrophosphate, triphosphate or salt therof and the remaining group of $Y_1$, $Y_2$ or $Y_3$ represents a hydroxyl group. The nontoxic salts of these phosphates are useful as an antileukemialagent for mice which is soluble in water and has high stability.

25 Claims, No Drawings

CYTIDINE NUCLEOTIDE DERIVATIVES

BACKGROUND OF THE INVENTION

1. Field of the Invention

The present invention relates to specific $N^4$-acyl-$\beta$-D-arabinofuranosylcytosine phosphates useful as water-soluble antileukemialagent for mice having high stability and also to specific $N^4$-acyl-1-$\beta$-D-ribofuranosylcytosine phosphates which are intermediates in the production of the above-described arabinofuranosylyctosine phosphates.

2. Description of the Prior Art

Cytosine arabinoside is one of the most effective known antileukemial agents. However, since the biological half life of the medicament is short, due primarily to the fact that it is readily excreted and readily metabolized, complicated administration methods are requied to provide the full effect of the medicament to patients. Furthermore, since the medicament is readily converted into uracil arabinoside, which possesses no antileukemial activity, by deamination with deoxycytidine deaminase, the medicament is ineffective for patients having high deaminose activity.

2,2'-anhydrocytosine arabinoside is a derivative of cytosine arabinoside which possesses improved susceptibility to the deaminose (it shows high resistance to the deaminose). While this medicament itself does not have antileukemial activity, it is gradually hydrolyzed in the body to form cytosine arabinoside, which exhibits antileukemial activity. This medicament is, however, quite readily excreted, and thus the greater part of the medicament is excreted before it is converted into the effective cytosine arabinoside. Effectively, the biological half life of this derivative is as short as that of cytosine arabinoside. Thus, to obtain sufficient effects from this derivative as a medicament, it is necessary to daily administer large amounts (e.g., 700 mg/kg) to mice.

The inventors previously performed various investigations to discover more effective antileukemial agents for mice by selecting materials which would prolong the life of mice infected by the leukemia L-1210, using the method developed by the Drugs Research & Development Department of the National Cancer Institute of the United States for screening antitumour agents and, as a result, the inventors found that $N^4$-acylcytosine arabinoside, where the acyl group is a straight-chain saturated or unsaturated aliphatic acyl group having at least 14 carbon atoms, shows an improved biological half life as compared with those of cytosine arabinoside and 2,2'-anhydrocytosine arabinoside.

That is, the acyl derivative of cytosine arabinoside, where the acyl group is an aliphatic acyl group or an aromatic acyl group having less than 12 carbon atoms, possesses an antileukemial activity for mice almost the same as or only slightly inferior to that of cytosine arabinoside, but the acyl derivative wherein the acyl group is an aliphatic acyl group having at least 14 carbon atoms possesses a much longer biological half life and has a high stability as compared with those of cytosine arabinoside and 2,2'-anhydrocytosine arabinoside.

Therefore, only one or two administrations of the acyl derivative greatly increases the life of mice infected with leukemia L-1210. However, the acyl derivatives have the disadvantage that $N^4$-acylcytosine arabinoside, which has a suitable oleophilicity and a high effect on mice infected with leukemia L-1210, is insoluble in water.

On the other hand, phosphoric acid esters and cyclic phosphoric acid esters of cytosine arabinoside are known. However, the phosphoric acid esters of cytosine arabinoside are inferior to cytosine arabinoside in antileukemial activity for mice, and while the cyclic phosphoric acid esters of cytosine arabinoside may have the same or a superior antiviral acitivity as compared by cytosine arabinoside, it is greatly inferior to the latter in activity against L-1210 leukemia in mice.

5'-Phosphoric acid esters of $N^4$-acylcytosine arabinoside are also known, in which the acyl group of the amino group at the 4-position thereof has 1 - 12 carbon atoms, as are 3',5'-cyclic phosphoric acid esters thereof, in which the acyl group of the amino group at the 4-position thereof has 1 - 18 carbon atoms. However, the phosphoric acid esters of the acyl derivative in which the acyl group has 1 - 12 carbon atoms and the cyclic phosphoric acid esters of the acyl derivative in which the acyl group has 1 - 18 carbon atoms possess substantially no antileukemial activity, although the latter may have an antiviral activity. Further, the cyclic phosphoric acid ester of the acyl derivative shows high hydrophobicity and is insoluble in water as compared with the phosphoric acid ester of the acyl derivative.

SUMMARY OF THE INVENTION

One object of this invention is, therefore, to provide compounds which are soluble in water and useful as an antileukemial agent for mice having high stability, and to provide intermediates for the preparation thereof.

A specific object of this invention is to provide $N^4$-acylcytosine arabinoside derivatives useful as antileukemial agents for mice having high solubility in water and high stability and also to provide intermediates for the preparation thereof.

It has been found that the aforesaid objects of this invention are attained by a nucleotide derivative represented by the general formula:

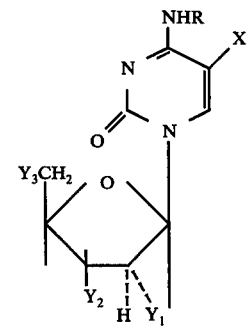

wherein R represents an acyl group having 14 - 22 carbon atoms and having an aliphatic acyl moiety; X represents a hydrogen atom, a halogen atom, an alkyl group having 1 - 4 carbon atoms, or a trifluoromethyl group; and at least one, but not all, of $Y_1$, $Y_2$, and $Y_3$ represents a phosphate, a pyrophosphate, a triphosphate, or a salt thereof, the balance of $Y_1$, $Y_2$ and $Y_3$ representing a hydroxyl group; or in case of ribosyl, $Y_1$ and $Y_3$, or $Y_2$ and $Y_3$ represent, at the same time, the aforesaid phosphate, pyrophosphate, triphosphate or salt thereof and the remaining group of $Y_1$, $Y_2$ or $Y_3$ represents a hydroxyl group; or in case of arabinosyl, $Y_1$ and $Y_2$, or $Y_2$ and $Y_3$ represent, at the same time, the aforesaid phosphate, pyrophosphate, triphosphate or salt thereof and the remaining group of $Y_1$, $Y_2$ or $Y_3$ represents a hydroxyl group.

DETAILED DESCRIPTION OF PREFERRED EMBODIMENTS OF THE INVENTION

The invention have found that novel salts of the nucleotide derivative having formula (I), where the furanosyl residue in the following general formula is arabinosyl (hereinafter, the salts are often referred to as Compound I) are soluble in water, have high antileukemial activity for mice and have high stability:

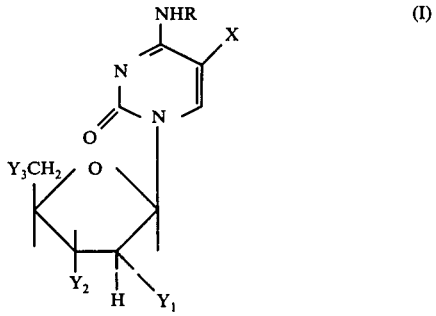

wherein R represents an acyl group having 14 – 22 carbon atoms and having an aliphatic acyl moiety; X represents a hydrogen atom, a halogen atom, an alkyl group having 1 – 4 carbon atoms, or a trifluoromethyl group; and at least one, but not all, of $Y_1$, $Y_2$, and $Y_3$ represents a phosphate, a pyrophosphate, a triphosphate, or a salt thereof, the balance of $Y_1$, $Y_2$ and $Y_3$ representing a hydroxyl group; or in case of ribosyl, $Y_1$ and $Y_3$, or $Y_2$ and $Y_3$ represent, at the same time, the aforesaid phosphate, pyrophosphate, triphosphate or salt thereof and the remaining group of $Y_1$, $Y_2$ or $Y_3$ represents a hydroxyl group; or in case of arabinosyl, $Y_1$ and $Y_2$, or $Y_2$ and $Y_3$ represent, at the same time, the aforesaid phosphate, pyrophosphate, triphosphate or salt thereof and the remaining group of $Y_1$, $Y_2$ or $Y_3$ represents a hydroxyl group.

Compound I can be prepared by arabinoacylating the novel nucleotide derivative represented by the formula where the furanosyl residue in the above general formula (I) is ribosyl (hereinafter referred to as Compound II).

In the following specification and claims the term "volume per unit weight" means milliliters per gram.

The arabinoacylation procedure will be explained below in detail.

Although compounds having general formula (II) are not known to show antileukemial activity, they are novel compounds useful as intermediates for the preparation of compounds of general formula (I).

The acyl group of the amino group at the 4-position of Compound I or II has 14 – 22 carbon atoms and an aliphatic acyl moiety. The acyl group can also have a neutral atom, group or moiety selected from an alicyclic hydrocarbon moiety having 4 – 12 carbon atoms, e.g., cyclodecane, cyclododecane, cyclododecene, cycloheptane, cycloheptene, cyclohexane, cyclohexene, cyclooctane, cyclooctene, cyclopentane, cyclopentene, adamantane and norbornane; an aromatic hydrocarbon moiety comprising 6 – 10 carbon atoms having one benzene ring, e.g., benzene, toluene, ethylbenzene and butylbenzene; a halogen atom, e.g., a fluorine atom, a chlorine atom, a bromine atom or an iodine atom; hydroxyl; mercapto; nitro; an N-dialkylamino group having 2 – 6 carbon atoms, e.g., N-dimethylamino, N-diethylamino, N-dipropylamino; epoxy (which means an oxygen atom bonded between two atoms in the form of a cyclic ether such as

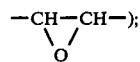

carbonyl; an alkoxy group having 1 – 20 carbon atoms, e.g., methoxy, ethoxy and butoxy; a thioalkoxy group having 1 – 20 carbon atoms, e.g., thiomethoxy (or methylthio), thioethoxy (or ethylthio) and thiobutoxy (or butylthio); phenoxy, thiophenoxy; and a carboxyalkyl group having 2 – 3 carbon atoms, e.g., carboxymethyl and carboxyethyl.

Typical examples of the acyl group of the amino group at the 4-position of the compound are a myristoyl group, an n-pentadecanoyl group, a palmitoyl group, margaroyl group, a stearoyl group, a nonadecanoyl group, an arachidoyl group, an n-heneicosadoyl group, a behenoyl group, an oleoyl group, an elaidoyl group, a behenoloyl group, a linoleoyl group, a linolenoyl group, a cyclohexyllauroyl group, a phenyllauroyl group, an adamantanebutyryl group, a 12-chlorostearoyl group, an ω-hydroxystearoyl group, an ω-mercaptostearoyl group, an ω-nitrostearoyl group, an ω-diethylaminostearoyl group, a 12,13-epoxy-9-octadecenoyl group, a 4-oxostearoyl group, an ethyloxystearoyl group, a thioethoxystearoyl group, a phenoxydecanoyl group, a thiophenoxydecanoyl group, and an ethylcarboxymargaroyl group.

Among the acyl groups illustrated above, acyl groups which are oleophilic are most preferred for their antileukemial activity. Examples of such acyl groups of high antileukemial activity are a palmitoyl group, a margaroyl group, a stearoyl group, a nonadecanoyl group, an arachidoyl group, a heneicosanoyl group and a behenoyl group. Among these groups, a behenoyl group is most preferred since this group shows very low toxicity.

The 5-position of Compound I or II may be unsubstituted or may be substituted with a halogen atom, an alkyl group having 1 – 4 carbon atoms, or a trifluoromethyl group. The halogen atom is a fluorine atom, a chlorine atom, a bromine atom or an iodine atom, and the alkyl group having 1 – 4 carbon atoms is a methyl group, an ethyl group, an n-propyl group, an isopropyl group, an n-butyl group, an isobutyl group or a tert-butyl group.

Among the compounds shown by formula (I), compounds unsubstituted at the 5-position thereof possess the greatest effect in prolonging the life of mice infected with L-1210 leukemia, i.e., compounds of formula (I) having a substituent at the 5-position thereof may have antiviral activity or activity against solid cancers, but are slightly inferior to compounds unsubstituted at the 5-position in prolonging the life of mice infected with L-1210 leukemia.

Compound I has been esterified at the 2'-position, the 3'-position or the 5'-position, or at the 2'- and 3'-positions, or at the 3'- and 5'-positions. The position of the monoester may be at the 2'-position, 3'-position, or 5'-position thereof, but the 5'-position is most preferred since the position can be most readily esterified. The positions of the diester may be the 2'- and 3'-positions or the 3'- and 5'-positions, but the 3'- and 5'-positions are more preferred than the 2'- and 3'-positions from the viewpoint of ease of esterification.

Examples of esters of Compound I or II are a phosphoric acid ester, a pyrophosphoric acid ester and a triphosphoric acid ester.

The compounds of this invention represented by general formula (I) can be administered as, for example, the monosodium salts or disodium salts thereof to increase their affinity for water.

Processes of producing the compounds of this invention will now be described.

The process can be summarized as follows:

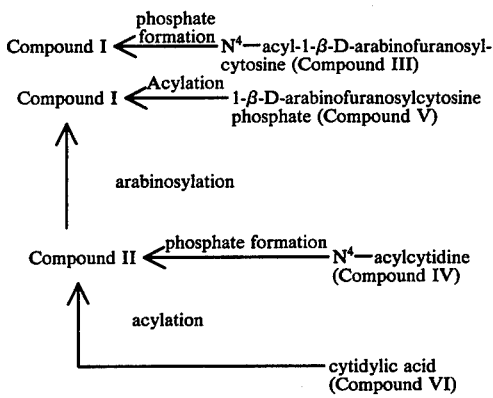

One process for producing Compound I from Compound II by arabinosylation may be carried out by refluxing Compound II at atmospheric pressure in a mixed solvent of 5 – 20 molar times the amount of Compound II of phosphorus oxychloride and a molar amount equivalent to Compound II of t-butyl alcohol for 1 – 2 hours and, subsequently, permitting the above product to stand in 10 – 100 volumes, per unit weight of the product, of a 2% sodium bicarbonate solution at atmospheric pressure and at 10°–30° C for 1 – 20 hours.

Another such arabinosylation process may be carried out by refluxing Compound II at atmospheric pressure with 1 – 20 molar times the amount of Compound II of thionyl chloride in 25 – 100 molar times the amount of Compound II of dioxane and thereafter following with the treatment with an alkaline solution as described above.

Furthermore, Compound I or II can be produced from Compound V (1-β-D-arabinofuranosylcytosine phosphate) or VI (cytidylic acid or cytidine phosphate) by reacting Compound V or VI with 0.9 – 1.4 molar times the amount of the nucleoside of an acylation agent in 1 – 100 volumes per unit weight of the nucleoside of a solvent or solvents at atmospheric pressure, at 0° C to the boiling point of the solvent(s) for 5 minutes to 20 hours, or with 1 – 100 molar, preferably 2-3 molar, times the amount of the nucleoside of an acyl anhydride, plus an acylation agent, in a completely water-miscible organic solvent containing an excess of water, as will be explained later in detail.

Compounds V and VI are known compounds and processes for their production are also well known. For example:

(1) Cytidine and 1-β-D-arabinofuranosylcytosine are commercially available.

(2) Processes for producing the 5-halogen substituted forms of cytidine and 1-β-D-arabinofuranosylcytosine are described in P. C. Srivastava et al., Experienta, Vol. 26, 220 (1970); M. W. Woods et al., Oncology, Vol. 23, 1 (1969); M. Hartman et al., German (East) Pat. No. 69,813; J. H. Hunter, French Pat. No. 1,513,754; and R. G. Duschinsky et al., Swiss Pat. No. 500,203.

(3) Processes for producing the 5-alkyl group (having 1 – 4 carbon atoms) or trifluoromethyl group substituted products of cytidine and 1-β-D-arabinofuranosylcytosine are described in T. D. Kulikowsky et al., Acta Biochim. Pol., Vol. 18, 209 (197).

(4) Processes for producing the 2'-phosphate, 3'-phosphate or 5'-phosphate of cytidine, 1-β-D-arabinofuranosylcytosine and their 5-substituted products described above are described in Khorane et al., Journal of American Chemical Society, Vol. 86, 4188 (1964); Wechter et al., Journal of Medicinal Chemistry, Vol. 10, 762 (1967); Japanese Pat. Publication No. 30,706/72; and Tetrahedron Letters, No. 22, 1965 (1965).

(5) Processes for producing the 2',5'-diphosphate or the 3',5'-diphosphate of cytidine and the 5-substituted products described above are described in The Annual Report of Takeda Research Institute, Vol. 23, 1 (1964). The 2',3'-diphosphates of cytidine and the 5-substituted products thereof cannot be synthesized because of stereo-hindrance.

(6) Processes for producing the 2',3'-diphosphate or 3',5'-diphosphate of 1-β-D-arabinofuranosylcytosine and the 5-substituted products described above are described in Smrt et al., Collection of Czechoslovak Chemical Communication; and Dekker et al., Journal of Organic Chemistry, Vol. 32, 816 (1967). The 2',5'-diphosphate of the nucleoside cannot be synthesized because of stereo-hindrance.

(7) Processes of further phosphating the phosphates described in (5) and (6) above to the pyrophosphate (2'-,3'-, 5'-, 2',5'-di, or 3',5'-di-pyrophosphate of cytidine and the 5-substituted products and the 2'-,3'-, 5'-, 2',3'-di, or 3',5'-di-pyrophosphate of 1-β-D-arabinofuranosylcytosine and the 5-substituted products thereof) are described in T. Sowa et al., German Offenlegungsschrift, No. 1,014,440; A. M. Michelson, J. Chem. Soc., 1957 (1958); M. Smith et al., J. Am. Chem. Soc., Vol 80, 1141 (1958); and R. W. Chambers et al., J. Am. Chem. Soc., Vol. 80, 3749 (1958).

(8) Processes of further phosphating the pyrophosphate described at (7) to the triphosphate (2'-,3'-,5'-, 2',5'-di, or 3',5'-di-triphosphate of cytidine and the 5-substituted products thereof and 2',3',5'-, 2',3'-di, or 3',5'-di-triphosphates of 1-β-D-arabinofuranosylcytosine and the 5-substituted products thereof) are described in T. Sowa et al., German Offenlegungsschrift No. 1,014,440; M. Smith et al., J. Am. Chem. Soc., Vol. 80, 1141 (1958); R. W. Chambers et al., J. Am. Chem. Soc., Vol. 80, 3749 (1958); and A. M. Michelson, Biochim. Biophys. Acta., Vol. 91, 1 (1964).

As earlier indicated, Compound V and Compound VI can be acylated to provide Compound I. The following discussion sets forth in great detail acylation procedures which can be used.

The acylation agent is selected from fatty acids, salts of fatty acids and reactive derivatives of fatty acids.

Examples of the fatty acid used for acylating Compound V or VI described above are myristic acid, pentadecanoic acid, palmitic acid, margaric acid, stearic acid, nonadecanoic acid, arachidic acid, heneicosanic acid, behenic acid, tetradecenoic acid, hexadecatrienoic acid, peteroselinic acid, oleic acid, linoleic acid, linolenic acid, 6,9,12-octadecatrienoic acid, eicosenoic acid, eicosadienoic acid, eicosatrienoic acid, arachidonic acid, cyclohexyllauric acid, phenyllauric acid, adamantanebutyric acid, 12-chlorostearic acid, ω-hydroxystearic acid, ω-mercaptostearic acid, ω-nitrostearic acid, ω-diethylaminostearic acid, 12,13-epoxy-9-octadecenoic acid, 4-oxostearic acid, ethyloxystearic acid, thioethoxystearic acid, phenoxydecanoic acid, thiophenoxydecanoic acid and ethylcarboxymargaric acid.

As useful salts of such fatty acids for the acylation, there can be illustrated alkali metal salts, alkaline earth metal salts, ammonia salts, and salts with organic bases such as trimethylamine, dichlorohexylamine, choline, and ethanolamine.

Examples of the reactive derivatives of the fatty acid used for the acylation of the fatty acid are acyl halides, acid anhydrides, amides, and esters. Specific examples of particularly useful reactive derivatives are acyl chlorides; acyl azides; acid anhydrides such as mixed anhydrides of the fatty acid and an alkyl phosphate (e.g., methyl phosphate), mixed anhydrides of the fatty acid and benzyl phosphate, mixed anhydrides of the fatty acid and a halophosphate, mixed anhydrides of the fatty acid and a dialkyl phosphite (e.g., dimethyl phosphite), mixed anhydrides of the fatty acid and a sulfite, mixed anhydrides of the fatty acid and a thiosulfate, mixed anhydrides of the fatty acid and a sulfate, mixed anhydrides of the fatty acid and an alkyl carbonate (e.g., ethyl carbonate), mixed anhydrides of the fatty acid and an aliphatic carboxylic acid (e.g., formic acid), mixed anhydrides of the fatty acid and an aromatic carboxylic acid (benzoic acid) and symmetric acid anhydrides (or anhydrides of the fatty acid); amides of the fatty acid and imidazole, etc.; and esters such as cyanomethyl ester, p-nitrophenyl ester, propargyl ester, carboxymethyl thioester, biphenyl ester, methoxy methyl ester, pyranyl ester, phenyl thioester, and N-hydroxy succinimide. Among the aforesaid reactive derivatives of the fatty acid, anhydrides of the fatty acid and fatty acid chlorides are particularly preferred.

When the acylation of Compound V or VI to Compound I is performed with a fatty acid in form of the free acid or a salt thereof, it is necessary to carry out the acylation in the presence of 1 - 100 molar times the amount of the nucleotide of a condensing agent such as, for example, N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyl-di-(2-methylimidazole), pentamethylene ketene, N-cyclohexylimine, diphenylketene-N-cyclohexylimine, alkoxyacetylene (e.g., methoxyacetylene), tolylalkoxy-1-chloroethylene, tetraalkyl phosphites (e.g., ethyl phosphite), N-ethyl-o-phenylisoxazolium-3'-sulfonate, ethyl polyphosphate or isopropyl polyphosphate.

The acylation reaction is usually carried out in a solvent. Examples of preferred solvents are hydrophilic solvents such as dioxane, acetone, acetonitrile, tetrahydrofuran, N,N-dimethylformamide, N,N-dimethylacetamide, tetramethylurea, dimethyl sulfoxide, hexamethyl phosphoramide, tetramethylenesulfone (Sulfolane), propylene carbonate, nitrobenzene, nitromethane, dimethyl cyanamide, fumaric acid, acetic acid, pyridine, methanol and ethanol.

These hydrophilic solvents may be used as a mixture with 1 - 100 molar times the amount of the fatty acid anhydride of water, if desired. In this case, water acts as a solvent for Compound V and Compound VI and also decomposes excess acylating agent. When chloroform, ethylene chloride, tetrahydrofuran, ethyl acetate, etc., are used as the solvent, the reaction system is heterogeneous, as the nucleotide is insoluble in the solvent.

Also, depending on the kind of reactive derivative of the fatty acid employed (e.g., acyl halide), the acylation may be carried out in the presence of 1 - 500 molar times the amount of the reactive derivative of the fatty acid of a base such as an alkali metal carbonate, a trialkylamine, pyridine, etc. If the base or the aforesaid condensing agent is a liquid, it can also be used as the solvent in 10 - 100 volumes per unit weight of Compound V or Compound VI. There is no particular limitation on the acylation temperature, but it is preferred that the reaction be carried out at temperatures from 0° C to the boiling point of the solvent used. When the base is the solvent, the bases boiling point determines the maximum reaction temperature.

The reaction product can be recovered from the reaction mixture in a conventional manner. For example, after reaction the solvent of the reaction mixture is evaporated at 0.1 to 0.5 atmospheric pressure at 40° - 60° C. After evaporation 10 - 50 volumes per unit weight of the residue of water is added to the residue to precipitate the reaction product at 0° C. The precipitate formed is collected by centrifuging at 4,000 r.p.m. for 1 - 10 hours. 10 - 50 volumes per unit weight of the precipitate of water is again added to wash out unreacted and reacted acylating agent, unreacted Compound V and Compound VI and the system centrifuged as described above. Then, 100 - 500 volumes per unit weight of the reaction product of n-hexane is added, followed by refluxing, whereafter the mixture is cooled and filtered. The reaction product thus recovered is recrystalized from hot ethanol.

Among the aforesaid acylation processes, a process in which the symmetric acid anhydride of the fatty acid is reacted with the nucleoside in a completely water-miscible organic solvent containing an excess of water is particularly preferred, as in this case the $N^4$-position can be selectively acylated at good yields.

Examples of the symmetric fatty acid anhydride used are myristic anhydride, pentadecanoic anhydride, palmitic anhydride, stearic anhydride, nonadecanoic anhydride, arachidic anhydride, heneicosanic anhydride, behenic anhydride, tetradecenoic anhydride, hexadecatrienoic anhydride, peteroselinic anhydride, oleic anhydride, linoleic anhydride, linolenic anhydride, 6,9,12-octadecatrienoic anhydride, eicosenoic anhydride, eicosadienoic anhydride, eicosatrienoic anhydride, arachidonic anhydride, cyclohexyllauric anhydride, phenyllauric anhydride, adamantanebutyric anhydride, 12-chlorostearic anhydride, ω-hydroxystearic anhydride, ω-mercaptostearic anhydride, ω-nitrostearic anhydride, ω-diethylaminostearic anhydride, 12,13-epoxy-9-octadecanoic anhydride, 4-oxostearic anhydride, ethyloxystearic anhydride, thioethoxystearic anhydride, phenoxydecanoic anhydride, thiophenoxydecanoic anhydride and ethylcarboxymargaric anhydride.

Examples of completely water-miscible organic solvents used are dioxane, N,N-dimethylacetamide (DMA), N,N-dimethylformamide (DMF), dimethylsulfoxide (DMSO), tetrahydrofuran (THF), methanol and ethanol.

In more detail, the symmetric anhydride of the fatty acid is added to the reaction system in an amount greater than equimolar, preferably 2 – 3 molar times, the amount of the nucleoside, and water is added thereto in an amount greater than equimolar, preferably 20 – 100 molar times, the amount of the symmetric anhydride of the fatty acid. An organic solvent miscible with water, such as dioxane, dimethylformamide, dimethyl sulfoxide, etc., is added to the reaction system until the reaction system becomes homogeneous. The amount of the organic solvent required becomes larger as the carbon number of the symmetric anhydride of the fatty acid becomes higher, but if the amount of the solvent is too large, the nucleotide will be precipitated; in such a case the precipitated nucleotide can be redissolved by heating the reaction system.

The symmetric anhydride of the fatty acid serves as a source for supplying the acyl group and the water helps to prevent the hydroxyl group of Compound V and VI from being acylated.

The reaction pressure is atmospheric and the reaction temperature is usually from 0° C to the boiling point of the solvent, preferably from room temperature to 80° C. The reaction period is 24 – 48 hours at room temperature, and 3 – 5 hours at 70° – 80° C. Since the nucleotide differs from $N^4$-acyl-nucleotide in solubility in the solvent used, the end point of the reaction can be detected using an ultraviolet lamp (2537 A) after developing a part of the reaction mixture by means of thin layer chromatography.

After the reaction is completed, water in an amount of 5 – 100 volumes per unit weight of the acyl anhydride is added to the reaction mixture to completely decompose the symmetric anhydride of the fatty acid and then the reaction mixture is concentrated under reduced pressure (0.1 – 0.5 atmospheric pressure at 40° – 60° C) to remove the solvent. Reduced pressure can cause the solvent to evaporate at 40° – 60° C below the boiling point of solvent at atmospheric pressure. If necessary, a solvent which has no substantial solvating effect on the reaction product, such as water, is added to the residue to precipitate the reaction product. The precipitate formed is collected by filtration, washed with water to remove unreacted acid anhydride, unreacted nucleotide, and carboxylic acid formed in the reaction, and then completely dehydrated.

A large amount (5 – 500 volumes per unit weight of the precipitate) of a nonpolar solvent such as n-hexane, benzene, cyclohexane, n-pentane, cyclopentane, toluene, xylene, ethyl acetate, ether, etc., is then added to the precipitate followed by refluxing at atmospheric pressure, whereafter the mixture is cooled and filtered. The crude $N^4$-acylnucleotide thus recovered is recrystallized from an organic solvent, i.e., a solvent whose solubility for $N^4$-acyl nucleotide increases with elevations in temperature, such as hot ethanol, hot acetone, hot chloroform, hot methanol, by cooling the solvent to 0° – 25° C, or purified by means of column chromatography using silica gel and a chloroform-methanol mixed solvent.

The reaction product can be identified by its infrared absorption spectrum, ultraviolet absorption spectrum, nuclear magnetic resonance spectrum and by elementary analysis. The ultraviolet absorption spectrum shows the presence of the $N^4$-acylcytosine moiety, while the infrared absorption spectrum shows the absorptions of the $N^4$-acylamide and phosphate ester.

In addition to the aforesaid processes where the phosphoric acid ester (Compound V or VI) is used as the starting material, Compound I or II in which the ester is a phosphate can be also obtained by reacting $N^4$-acyl-5-substituted or unsubstituted-1-$\beta$-D-arabinofuranosylcytosine or $N^4$-acyl-5-substituted or unsubstituted-1-$\beta$-D-ribofuranosylcytosine (Compound III or IV) with 1 – 10 molar times the amount of Compound III or IV of a phosphating agent at atmospheric pressure at 0° – 30° C for 5 minutes to 4 hours, as shown below. The derivative in which the ester is a pyrophosphate can be obtained by further reacting the phosphate thus obtained with the phosphating agent, e.g., 1 – 10 molar times the amount of the phosphate of dibenzyl phosphate chloride in 1 – 10 molar times the amount of the phosphate of tri-n-octylamine, 10 – 100 volumes per unit weight of the phosphate of dioxane and 5 – 50 volumes per unit weight of the phosphate of benzene at atmospheric pressure at 0° – 30° C for 5 minutes to 3 hours, and then by reducing the product with hydrogen gas in the presence of 0.01 to 0.1 molar times the amount of the product of palladium chloride at atmospheric pressure at 0° – 30° C for 5 minutes to 4 hours, and the derivative in which the ester is a triphosphate can be obtained by further reacting the pyrophosphate thus obtained with the phosphating agent by a similar procedure as described for the phosphation of the phosphate to the pyrophosphate.

$N^4$-acyl-5-substituted or unsubstituted-1-$\beta$-D-arabinofuranosylcytosine or $N^4$-acyl-5-substituted or unsubstituted-1-$\beta$-D-ribofuranosylcytosine (Compound III or IV) as the starting material can be obtained by reacting the known 5-substituted or unsubstituted-1-$\beta$-D-arabinofuranosylcytosine or 5-substituted or unsubstituted-1-$\beta$-D-ribofuranosylcytosine (shown in the aforesaid literature) with the acylating agent described with respect to the acylation of Compound V or VI as disclosed in Japanese Pat. Application Laid Open No. 18,482/75.

Examples of phosphating agents used for the aforesaid reactions are phosphorus oxychloride, tetrachloropyrophosphoric acid, dibenzylphosphoric acid chloride, dimorpholinophosphoric acid chloride, etc.

In the selective phosphation of the hydroxyl group at the 5'-position with phosphorus oxychloride, it is preferred to carry out the reaction in the presence of a reaction aid such as an alcohol and a tertiary organic amine at atmospheric pressure at 0° – 30° C for 5 minutes to 4 hours. Examples of the alcohols used for this purpose are aliphatic alcohols such as methanol, ethanol, 1-propanol, propargyl alcohol, allyl alcohol, n-butanol, etc., and examples of tertiary organic amines are pyridine, triethylamine, trimethylamine, tri-n-propylamine, tri-n-butylamine, tri-n-octylamine, tripropargylamine, etc. The preferred mixing ratio of raw material and reagents is as follows: the molar ratio of the raw material:phosphorus oxychloride:alcohol:tertiary organic amine is 0.8 – 1:2:1:1. If the ratio deviates from the above value, the product yield decreases. Solvents are not used; the presence of the phosphorus oxychloride, alcohol and tertiary organic amine is sufficient.

When the aforesaid reaction aid is not used, the hydroxyl groups at the 3'-position and the 5'-position are phosphated. When dibenzylphosphoric acid chloride, dimorpholinophosphoric acid chloride, etc., are used as the phosphating agent, it is necessary to remove each protective group, such as dibenzyl or dimorpholino, after the phosphation. A protective group can be removed by a catalytic reduction using palladium when dibenzylphosphoric acid chloride is used (e.g., by reducing the product with hydrogen gas in the presence of 0.01 – 0.1 molar times the amount of the product of palladium chloride at atmospheric pressure at 0° – 20° C for 5 minutes to 4 hours) or under slightly acidic conditions (e.g., pH 3 – 5) using a proton-type ion-exchange resin (e.g., any resin having carboxyl groups), etc., when dimorpholinophosphoric acid chloride is used.

There is no particular limitation on the reaction temperature for the phosphating reaction, but lower temperatures (in the range of from room temperature to below 0° C) are generally preferred. While the phosphating agent itself may be used as the solvent in this reaction, it is particularly preferred to use an organic solvent of high polarity. Examples of such organic solvent are pyridine, dioxane, acetonitrile, acetone, methanol, tetrahydrofuran, etc. In particular, the use of pyridine is preferred as pyridine acts as an acceptor for hydrogen chloride formed during the reaction.

The progress of the phosphating reaction can be analyzed using thin layer chromatography (silica gel and a chloroform-methanol mixed solvent, e.g., a 1:1 molar ratio chloroform-methanol mixed solvent). The reaction is completed when traces of the raw material cannot be detected by thin layer chromatography.

After the reaction is completed, the phosphating agent can be decomposed with 100 – 500 molar times the amount of the phosphating agent of water or an alcohol such as methanol, at atmospheric pressure at 0° – 5° C for 5 minutes – 20 hours, etc. With a phosphating agent free of a protective group, such as phosphorus oxychloride, tetrachloropyrophosphoric acid, etc., it is necessary to hydrolyze the phosphating agent with water. Hydrogen chloride formed in the reaction and the decomposition can be neutralized using an equivalent amount (calculated amount; to the hydrogen chloride formed) of a weak alkali such as sodium hydrogen carbonate, potassium hydrogen carbonate, etc., at atmospheric pressure, at 0° – 5° C for 1 – 5 minutes, although neutralization is not always necessary.

The crude reaction product is precipitated during the course of the decomposition of the phosphating agent and, if hydrogen chloride must be neutralized, during the course of neutralizing hydrogen chloride formed. If the reaction product does not precipitate, it can be precipitated by further adding water to the reaction mixture or a reaction product precipitate can be obtained by concentrating the reaction mixture at low pressure (0.1 – 0.5 atmospheric pressure) and at 25° – 30° C. The precipitates thus formed can be recovered by filtration or centrifugal separation in a conventional manner.

The crude reaction product thus obtained can be purified by column chromatography (silica gel and 1,000 volumes per unit weight of crude reaction product of a chloroform-methanol mixed solvent) or recrystallization (10 – 20 volumes per unit weight of crude reaction product of a dioxane-water mixed solvent, ethanol, etc.).

The reaction product can be analyzed by its ultraviolet absorption spectrum, infrared absorption spectrum, nuclear magnetic resonance spectrum and by elementary analysis. The ultraviolet absorption spectrum shows the presence of the $N^4$-acylcytosine moiety and the infrared absorption spectrum shows the absorptions of the $N^4$-acylamide and phosphate ester. The presence of the 5'-phosphate can be detected by its nuclear magnetic resonance spectrum due to the fact that the 5'-methylene group shows about a 0.5 ppm lower magnetic field shift as compared with the starting material.

The compound of this invention represented by formula (I) prepared as described above forms a salt with a base at the phosphate group of the compound, whereby the compound of this invention becomes soluble in water and the pharmacological utility thereof is increased. More specifically, the compound of formula (I) can be easily converted into the non-toxic metal salts such as the sodium salt, potassium salt, calcium salt or aluminum salt thereof; the non-toxic ammonium salt thereof; or non-toxic substituted ammonium salts with an amine such as a trialkylamine, procaine, dibenzylamine, N-benzyl-β-phenethylamine, N,N'-dibenzylethylene diamine, dehydrobiethylamine, an N-lower alkyl piperidine, arginine, lysine, choline, etc.

The non-toxic salts of the compound of formula (I) are obtained by reacting the compound of formula (I) with an equimolar amount of the hydrogen carbonate, hydroxide or mineral acid addition salt of the non-toxic metal, ammonium, or non-toxic amine as described above in an aqueous solvent, and then removing the solvent.

The illustrated non-toxic metal salts, ammonium salts, and substituted ammonium salts of the compound of formula (I) of this invention are soluble in water. Thus, by adding, if desired, an isotonic agent, an analgesic, an antibacterial agent, and/or an antifungal agent to an aqueous solution of a salt of the compound of formula (I) of this invention, an aqueous preparation of the compound of formula (I) of this invention suitable for injection can be prepared, which can be, e.g., administered by intravenous injection, subcutaneous injection, intramuscular injection, intraperitoneal injection or interamedullary injection.

The invention will now be illustrated in more detail by several non-limiting examples. All processings are at atmospheric pressure unless otherwise indicate.

EXAMPLE 1

To 3.23 g of 1-β-D-arabinofuranosylcytosine-5'-phosphate was added 20 ml of water and, after adding thereto 300 ml of dioxane and 13.6 g of stearic anhydride, the system was reacted for 5 hours at 80° C. The reaction mixture was then cooled to 5° C and 1 liter of water added thereto to form a precipitate, which was recovered by filtration, washed with water and dried in a vacuum desiccator. The thus dried precipitate was washed with n-hexane and recrystallized from ethyl acetate to provide 5.1 g of $N^4$-stearoyl-1-β-D-arabinofuranosylcytosine-5'-phosphate.

Yield of the product: 86.6%; melting point: 215°–218° C. (decomp.); molecular weight: 589.

| | Elementary analysis for $C_{27}H_{28}O_9N_3P$ | | |
|---|---|---|---|
| | C | H | N |
| Calculated: | 54.99% | 8.21% | 7.13% |
| Found: | 54.86% | 8.26% | 7.09% |
| Ultraviolet absorption spectrum: 248,299 mμ | | | |

5 ml of concentrated aqueous ammonia solution (28%) was added to a part (50 mg) of the product, and the mixture was heated for 3 hours at 60° C. 10 ml of methanol was added to the resulting mixture and dried by evaporating solvent at 0.5 atmospheric pressure at 50° C for 3 hours to recover 1-β-D-arabinofuranosylcytosine-5'-phosphate.

EXAMPLE 2

1.18 g of $N^4$-stearoyl-1-$\beta$-D-arabinofuranosylcytosine-5'-phosphate was suspended in a mixed solvent of 50 ml of water and 50 ml of ethanol and, after adding to the suspension 0.168 g of sodium hydrogen carbonate, the mixture was vigorously stirred, whereby the sodium hydrogen carbonate disappeared to give a homogeneous colloidal solution. By lyophilizing the solution, 1.16 g of $N^4$-stearoyl-1-$\beta$-D-arabinofuranosylcytosine-5'-phosphate monosodium salt was obtained as a white solid.

Similarly, 1.10 g of $N^4$-stearoyl-1-$\beta$-D-arabinofuranosylcytosine-5'-phosphate was suspended in a mixed solvent of 70 ml of water and 135 ml of ethanol and, after adding 0.335 g of sodium hydrogen carbonate to the suspension, the resulting mixture was stirred vigorously for 3 hours, whereby sodium hydrogen carbonate disappeared to provide a homogeneous colloidal solution. By lyophilizing the solution, 1.15 g of $N^4$-stearoyl-1-$\beta$-D-arabinofuranosylcytosine-5'-phosphate disodium salt was obtained as a white solid.

EXAMPLE 3

By reacting corresponding 1-$\beta$-D-arabinofuranosylcytosine-5'-phosphates and other fatty acid anhydrides as earlier described in detail instead of stearic anhydride in the same manner as in Example 1, the following products were obtained. By following the same reaction scheme except using 5'-cytidylic acid instead of 1-$\beta$-D-arabinofuranosylcytosine-5'-phosphate, the products also shown below were also obtained:

$N^4$-Pentadecanoyl-1-$\beta$-D-arabinofuranosylcytosine-5'-phosphate: Yield: 82.4%, molecular weight: 547.
Elementary analysis for $C_{24}H_{42}O_9N_3P$: Calculated: C 52.63%; H 7.68%; N 7.68%. Found: C 52.60%; H 7.65%; N 7.65%.
Ultraviolet absorption spectra: 248 and 299 m$\mu$ $N^4$-Palmitoyl-1-$\beta$-D-arabinofuranosylcytosine-5'-phosphate: Yield: 83.8%, molecular weight: 561.
Elementary analysis for $C_{25}H_{44}O_9N_3P$: Calculated: C 53.45%; H 7.84%; N 7.49%. Found: C 53.40%; H 7.85%; N 7.50%.
Ultraviolet absorption spectra: 248 and 299 m$\mu$.

$N^4$-Margaroyl-1-$\beta$-D-arabinofuranosylcytosinz-5'-phosphate: Yield 85.3%, molecular weight 575.
Elementary analysis for $C_{26}H_{46}O_9N_3P$: Calculated: C 54.23%; H 8.00%; N 7.30%. Found: C 54.20%; H 8.05%; N 7.31%.
Ultraviolet absorption spectra: 248 and 299 m$\mu$ $N^4$-Nonadecanoyl-1-$\beta$-D-arabinofuranosylcytosine-5'-phosphate: Yield: 82.7%, molecular weight 603.
Elementary analysis for $C_{28}H_{50}O_9N_3P$: Calculated: C 55.69%; H 8.29%; N 6.96%. Found: C 55.65%; H 8.30%; N 6.95%.
Ultraviolet absorption spectra: 248 and 299 m$\mu$ $N^4$-Arachidoyl-1-$\beta$-D-arabinoylfuranosylcytosine-5'-phosphate: Yield: 84.5%, molecular weight 617.
Elementary analysis for $C_{29}H_{52}P_9N_3P$: Calculated: C 56.37%; H 8.43%; N 6.81%. Found: C 56.35%; H 8.40%; N 6.80%.
Ultraviolet absorption spectra: 248 and 299 m$\mu$ $N^4$-Heneicosanoyl-1-$\beta$-D-arabinofuranosylcytosine-5'-phosphate: Yield: 83.1%, molecular weight 631.
Elementary analysis for $C_{30}H_{54}O_9N_3P$: Calculated: C 57.02%; H 8.56%; N 6.66%. Found: C 57.01%; H 8.55%; N 6.65%.
Ultraviolet absorption spectra: 248 and 299 m$\mu$ $N^4$-Behenoyl-1-$\beta$-D-arabinofuranosylcytosine-5'-phosphate: Yield: 83.4%, molecular weight 645.
Elementary analysis for $C_{31}H_{56}O_9N_3P$: Calculated: C 57.65%; H 8.68%; N 6.51%. Found: C 57.62%; H 8.66%; N 6.54%.
Ultraviolet absorption spectra: 248 and 299 m$\mu$ $N^4$-Tricosanoyl-1-$\beta$-D-arabinofuranosylcytosine-5'-phosphate: Yield: 83.5%, molecular weight 659.
Elementary analysis for $C_{32}H_{58}O_9N_3P$: Calculated: C 58.23%; H 8.80%; N 6.37%. Found: C 58.24%; H 8.85%; N 6.35%.
Ultraviolet absorption spectra: 248 and 299 m$\mu$ $N^4$-Lignoceroyl-1-$\beta$-D-arabinofuranosylcytosine-5'-phosphate: Yield: 82.9%, molecular weight 673.
Elementary analysis for $C_{33}H_{60}O_9N_3P$: Calculated: C 58.84%; H 8.92%; N 6.24%. Found: C 58.82%; H 8.90%; N 6.25%.
Ultraviolet absorption spectra: 248 and 299 m$\mu$ $N^4$-Pentacosanoyl-1-$\beta$-D-arabinofuranosylcytosine-5'-phosphate: Yield: 82.9%, molecular weight 687.
Elementary analysis for $C_{34}H_{62}O_9N_3P$: Calculated: C 59.36%; H 9.01%; N 6.11%. Found: C 59.36%; H 9.01%; N 6.15%.
Ultraviolet absorption spectra: 248 and 299 m$\mu$ $N^4$-Serotoyl-1-$\beta$-D-arabinofuranosylcytosine-5'-phosphate: Yield: 85.1%, molecular weight 701.
Elementary analysis for $C_{35}H_{64}O_9N_3P$: Calculated: C 59.88%; H 9.13%; N 5.99%. Found: C 59.86%; H 9.11%; N 6.00%.
Ultraviolet absorption spectra: 248 and 299 m$\mu$ $N^4$-Heptacosanoyl-1-$\beta$-D-arabinofuranosylcytosine-5'-phosphate: Yield: 80.8%, molecular weight 715.
Elementary analysis for $C_{36}H_{66}O_9N_3P$: Calculated: C 60.42%; H 9.23%; N 5.87%. Found: C 60.45%; H 9.20%; N 5.90%.
Ultraviolet absorption spectra: 248 and 299 m$\mu$.

$N^4$-Montanoyl-1-$\beta$-D-arabinofuranosylcytosine-5'-phosphate: Yield: 82.3%, molecular weight 729.
Elementary analysis for $C_{37}H_{68}O_9N_3P$: Calculated: C 60.90%; H 9.33%; N 5.76%. Found: C 60.92%; H 9.35%; N 5.76%.
Ultraviolet absorption spectra: 248 and 299 m$\mu$ $N^4$-Myricoyl-1-$\beta$-D-arabinofuranosylcytosine-5'-phosphate: Yield: 80.0%, molecular weight 753.
Elementary analysis for $C_{39}H_{72}O_9H_3P$: Calculated: C 61.82%; H 9.51%; N 5.55%. Found: C 61.80%; H 9.50%; N 5.55%.
Ultraviolet absorption spectra: 248 and 299 m$\mu$ $N^4$-Ceroplatoyl-1-$\beta$-D-arabinofuranosylcytosine-5'-phosphate: Yield: 80.3%, molecular weight 827.
Elementary analysis for $C_{44}H_{82}O_9H_3P$: Calculated: C 63.84%; H 9.81%; N 5.08%. Found: C 63.85%; H 9.90%; N 5.10%.
Ultraviolet absorption spectra: 248 and 299 m$\mu$ $N^4$-$\omega$-Chlorostearoyl-1-$\beta$-D-arabinofuranosylcytosine-5'-phosphate: Yield: 68.3%, molecular weight 624.
Elementary analysis for $C_{27}H_{47}O_9N_3PCl$: Calculated: C 51.69%; H 7.72%; N 6.70%. Found: C 51.65%; H 7.75%; N 6.65%.
Ultraviolet absorption spectra: 248 and 299 m$\mu$ $N^4$-Palmitooleoyl-1-$\beta$-D-arbinofuranosylcytosine-5'-phosphate: Yield: 80.2%, molecular weight 559.
Elementary analysis for $C_{25}H_{42}O_9N_3P$: Calculated: C 53.64%; H 7.51%; N 7.51%. Found C 53.65%; H 7.50%; N 7.50%.
Ultraviolet absorption spectra: 248 and 299 m$\mu$ $N^4$-Oleoyl-1-$\beta$-D-arabinofuranosylcytosine-5'-phosphate: Yield: 80.7%, molecular weight 587.

Elementary analysis for $C_{27}H_{46}O_9N_3P$: Calculated: C 55.17%; H 7.84%; N 7.16%. Found: C 55.20%; H 7.85%; N 7.18%.

Ultraviolet absorption spectra: 248 and 299 mμ

$N^4$-Linoleoyl-1-β-D-arabinofuranosylcytosine-5'-phosphate: Yield: 80.2%, molecular weight 585.

Elementary analysis for $C_{27}H_{44}O_9N_3P$: Calculated: C 55.36%; H 7.52%; N 7.20%. Found: C 55.38%; H 7.52%; N 7.15%.

Ultraviolet absorption spectra: 248 and 299 mμ

$N^4$-Linolenoyl-1-β-D-arabinofuranosylcytosine-5'-phosphate: Yield: 80.9%, molecular weight 593.

Elementary analysis for $C_{27}H_{42}O_9N_3P$: Calculated: C 55.55%; H 7.20%; N 7.20%. Found: C 55.57%; H 7.21%; N 7.20%.

Ultraviolet absorption spectra: 248 and 299 mμ

$N^4$-Arachidonoyl-1-β-D-arabinofuranosylcytosine-5'-phosphate: Yield: 80.9%, molecular weight 609.

Elementary analysis for $C_{29}H_{44}O_9N_3P$: Calculated: C 57.12%; H 7.22%; N 6.90%. Found: C 57.10%; H 7.24%; N 6.91%.

Ultraviolet absorption spectra: 248 and 299 mμ

$N^4$-Myristoyl-5'-cytidylate: Yield: 82.2%, molecular weight 533.

Elementary analysis for $C_{23}H_{40}O_9N_3P$: Calculated: C 51.76%; H 7.50%; N 7.88%. Found: C 51.70%; H 7.54%; N 7.86%.

Ultraviolet absorption spectra: 248 and 299 mμ

$N^4$-Pentadecanoyl-5'-cytidylate: Yield: 82.5%, molecular weight 547.

Elementary analysis for $C_{24}H_{42}O_9N_3P$: Calculated: C 52.63%; H 7.68%; N 7.68%. Found: C 52.61%; H 7.65%; N 7.65%.

Ultraviolet absorption spectra: 248 and 299 mμ

$N^4$-Palmitoyl-5'-cytidylate: Yield: 83.1% molecular weight 561.

Elementary analysis for $C_{25}H_{44}O_9N_3P$: Calculated: C 53.45%; H 7.84%; N 7.49%. Found: C 53.41%; H 7.86%; N 7.52%.

Ultraviolet absorption spectra: 248 and 229 mμ

$N^4$-Margaroyl-5'-cytidylate: Yield: 84.6%, molecular weight 575.

Elementary analysis for $C_{26}H_{46}O_9N_3P$: Calculated: C 54.23%; H 8.00%; N 7.30%. Found: C 54.24%; H 8.06%; N 7.32%.

Ultraviolet absorption spectra: 248 and 299 mμ

$N^4$-Stearoyl-5'-cytidylate: Yield: 86.6%, molecular weight 589.

Elementary analysis for $C_{27}H_{48}O_9N_3P$: Calculated: C 54.98%; H 8.15%; N 7.13%. Found: C 54.99%; H 8.16%; N 7.10%.

Ultraviolet absorption spectra: 248 and 299 mμ

$N^4$-Nonadecanoyl-5'-cytidylate: Yield: 84.3%, molecular weight 603.

Elementary analysis for $C_{28}H_{50}O_9N_3P$: Calculated: C 55.69%; H 8.29%; N 6.96%. Found: C 55.64%; H 8.31%; N 6.94%.

Ultraviolet absorption spectra: 248 and 299 mμ

$N^4$-Arachidoyl-5'-cytidylate: Yield: 84.7%, molecular weight 617.

Elementary analysis for $C_{29}H_{52}O_9N_3P$: Calculated: C 56.37%; H 8.43%; N 6.81%. Found: C 56.37%; H 8.42%; N 6.80%.

Ultraviolet absorption spectra: 248 and 299 mμ

$N^4$-Heneicosanoyl-5'-cytidylate: Yield: 82.8%, molecular weight 631.

Elementary analysis for $C_{30}H_{54}O_9N_3P$: Calculated: C 57.02%; H 8.56%; N 6.66%. Found: C 57.05%; H 8.55%; N 6.64%.

Ultraviolet absorption spectra: 248 and 299 mμ

$N^4$-Behenoyl-5'-cytidylate: Yield: 83.3%, molecular weight 645.

Elementary analysis for $C_{31}H_{56}O_9N_3P$: Calculated: C 57.65%; H 8.68%; N 6.51%. Found: C 57.60%; H 8.65%; N 6.53%.

Ultraviolet absorption spectra: 248 and 299 mμ

$N^4$-Tricosanoyl-5'-cytidylate: Yield: 82.7%, molecular weight 659.

Elementary analysis for $C_{32}H_{58}O_9N_3P$: Calculated: C 58.23%; H 8.80%; N 6.37%. Found: C 58.25%; H 8.84%; N 6.36%.

Ultraviolet absorption spectra: 248 and 299 mμ

$N^4$-Lignoceroyl-5'-cytidylate: Yield: 82.7%, molecular weight 673.

Elementary analysis for $C_{33}H_{60}O_9N_3P$: Calculated: C 58.84%; H 8.92%; N 6.24%. Found: C 58.82%; H 8.91%, N 6.26%.

Ultraviolet absorption spectra: 248 and 299 mμ

$N^4$-Pentacosanoyl-5'-cytidylate: Yield: 82.3%, molecular weight 687.

Elementary analysis for $C_{34}H_{62}O_9N_3P$: Calculated: C 59.36%; H 9.02%; N 6.11%. Found: C 59.35%; H 9.00%; N 6.10%.

Ultraviolet absorption spectra: 248 and 299 mμ

$N^4$-Cerotoyl-5'-cytidylate: Yield: 8%, molecular weight 701.

Elementary analysis for $C_{35}H_{64}O_9N_3P$: Calculated: C 59.88%; H 9.13%; N 5.99%. Found: C 59.85%; H 9.13%; N 6.01%.

Ultraviolet absorption spectra: 248 and 299 mμ

$N^4$-Heptacosanoyl-5'-cytidylate: Yield: 80.9%, molecular weight 715.

Elementary analysis for $C_{36}H_{66}O_9N_3P$: Calculated: C 60.42%; H 9.25%; N 5.87%. Found: C 60.44%; H 9.25%; N 5.92%.

Ultraviolet absorption spectra: 248 and 299 mμ

$N^4$-Montanoyl-5'-cytidylate: Yield: 8%, molecular weight 729.

Elementary analysis for $C_{37}H_{60}O_9N_3P$: Calculated: C 60.90%; H 9.33%; N 5.76%. Found: C 60.92%; H 9.36%; N 5.77%.

Ultraviolet absorption spectra: 248 and 299 mμ

$N^4$-Myricoyl-5'-cytidylate: Yield: 80.2%, molecular weight 753.

Elementary analysis for $C_{39}H_{72}O_9N_3P$: Calculated: C 61.82%; H 9.51%; N 5.55%. Found: C 61.81%; H 9.50%; N 5.57%.

Ultraviolet absorption spectra: 248 and 299 mμ

$N^4$-Ceprastoyl-5'-cytidylate: Yield: 8%, molecular weight 827.

Elementary analysis for $C_{44}H_{82}O_9N_3P$: Calculated: C 63.84%; H 9.91%; N 5.08%. Found: C 63.86%; H 9.92%; N 5.09%.

Ultraviolet absorption spectra: 248 and 299 mμ

$N^4$-Hexatriacontanoyl-5'-cytidylate: Yield: 68.0%, molecular weight 981.

Elementary analysis for $C_{55}H_{104}O_9N_3P$: Calculated: C 67.28%; H 10.60%; N 4.28%. Found: C 67.25%; H 10.60%; N 4.30%.

Ultraviolet absorption spectra: 248 and 299 mμ

$N^4$-Palmitoleoyl-5'-cytidylate: Yield: 80.4%, molecular weight 559.

Elementary analysis for $C_{25}H_{42}O_9N_3P$: Calculated: C 53.64%; H 7.51%; N 7.51%. Found: C 53.64%; H 7.52%; N 7.50%.

Ultraviolet absorption spectra: 248 and 299 mμ

$N^4$-Oleoyl-5'-cytidylate: Yield: 80.4%, molecular weight 587.

Elementary analysis for $C_{27}H_{46}O_9N_3P$: Calculated: C 55.17%; H 7.84%; N 7.16%. Found: C 55.18%; H 7.85%; N 7.15%.

Ultraviolet absorption spectra: 248 and 299 mμ

$N^4$-Linoleoyl-5'-cytidylate: Yield: 80.7%, molecular weight 585.

Elementary analysis for $C_{27}H_{44}O_9N_3P$: Calculated: C 55.36%; H 7.52%; N 7.18%. Found: C 53.35%; H 7.50%; N 7.20%.

Ultraviolet absorption spectra: 248 and 299 mμ

$N^4$-Linolenoyl-5'-cytidylate: Yield: 80.4%, molecular weight 583.

Elementary analysis for $C_{27}H_{42}O_9N_3P$: Calculated: C 55.55%; H 7.20%; N 7.20%. Found: C 55.54%; H 7.22%; N 7.21%.

Ultraviolet absorption spectra: 248 and 299 mμ

$N^4$-Arachidonoyl-5'-cytidylate: Yield: 80.3%, molecular weight 609.

Elementary analysis for $C_{28}H_{44}O_9N_3P$: Calculated: C 57.12%; H 7.22%; N 6.90%. Found: C 57.14%; H 7.23%; N 6.90%.

Ultraviolet absorption spectra: 248 and 299 mμ.

EXAMPLE 4

3.23 g of 1-β-D-arabinofuranosylcytosine-5'-phosphate was dissolved in 30 ml of N,N-dimethylformamide and then 8.3 ml of pyridine was added to the solution. After further adding 3.38 g of adamantoyl chloride to the solution, the mixture was stirred for 8 hours at 60° C. The reaction mixture formed was concentrated under reduced pressure (0.5 atmospheric pressure) and 100 ml of ice water was added to the concentrate thus obtained followed by shaking whereby a white precipitate formed. The precipitate was recovered by filtration and dried under a vacuum. The resulting solid residue was added to about 100 ml of benzene and the system refluxed. After cooling, the system was filtered. The refluxing, cooling and filtering steps were then repeated twice and the solid residue recovered by filtration was dissolved in 50 ml of methanol with heating to 70° C and the solution allowed to cool to 25° C, whereby $N^4$-adamantoyl-1-β-D-arabinofuranosylcytosine-5'-phosphate was obtained as a white amorphous solid.

Yield: 41.0%, molecular weight 485. Elementary analysis for $C_{20}H_{28}O_9N_3P$: Calculated: C 49.47%; H 5.81%; N 8.66%. Found: C 49.43%; H 5.80%; N 8.65%.

Ultraviolet absorption spectra: 248 and 299 mμ

EXAMPLE 5

Following the procedure of Example 2, the following salts were produced from sodium hydrogen carbonate and the corresponding $N^4$-acyl-1-β-D-arabinofuranosylcytosine-5'-phosphates or $N^4$-acyl-5'-cytidylates instead of $N^4$-stearoyl-1-β-D-arabinofuranosylcytosine-5'-phosphates:

$N^4$-Myristoyl-1-β-D-arabinofuranosylcytosine-5'-phosphate monosodium and disodium ($C_{23}H_{39}O_9N_3PNa$ and $C_{23}H_{38}O_9N_3PNa_2$), $N^4$-myristoyl-5'-cytidylate monosodium and disodium ($C_{23}H_{39}O_9N_3PNa$ and $C_{23}H_{38}O_9N_3PNa_2$), $N^4$-palmitoyl-1-β-D-arabinofuranosylcytosine-5'-phosphate monosodium and disodium ($C_{25}H_{43}O_9N_3PNa$ and $C_{25}H_{42}O_9N_3PNa_2$), $N^4$-palmitoyl-5'-cytidylate monosodium and disodium ($C_{25}H_4O_9N_3ONa$ and $C_{25}H_{42}O_9N_3PNa_2$), $N^4$-margaroyl-1-β-D-arabinofuranosylcytosine-5'-phosphate monosodium and disodium ($C_{26}H_{45}O_9N_3PNa$ and $C_{26}H_{44}O_9N_3PNa_2$), $N^4$-margaroyl-5'-cytidylate monosodium and disodium ($C_{26}H_{45}O_9N_3PNa$ and $C_{26}H_{44}O_9N_3PNa_2$), $N^4$-stearoyl-5'-cytidylate monosodium and disodium ($C_{27}H_{47}O_9N_3PNa$ and $C_{27}H_{46}O_9N_3PNa_2$), $N^4$-nonadecanoyl-1-β-D-arabinofuranosylcytosine-5'-phosphate monosodium and disodium ($C_{28}H_{49}O_9N_3PNa$ and $C_{28}H_{48}O_9N_3PNa_2$), $N^4$-arachidoyl-1-β-D-arabinofuranosylcytosine-5'-phosphate monosodium and disodium ($C_{29}H_{51}O_9N_3PNa$ and $C_{29}H_{50}O_9N_3PNa_2$), $N^4$-montanoyl-1-β-D-arabinofuranosylcytosine-5'-phosphate monosodium and disodium ($C_{37}H_{67}O_9N_3PNa$ and $C_{37}H_{66}O_9N_3PNa_2$), $N^4$-palmitoleoyl-1-β-D-arabinofuranosylcytosine-5'-phosphate monosodium and disodium ($C_{25}H_{41}O_9N_3PNa$ and $C_{25}H_{40}O_9N_3PNa_2$), $N^4$-oleoyl-1-β-D-arabinofuranosylcytosine-5'-phosphate monosodium and disodium ($C_{27}H_{45}O_9N_3ONa$ and $C_{27}H_{44}O_9N_3PNa_2$), $N^4$-arachidonoyl-1-β-D-arabinofuranosylcytosine-5'-phosphate monosodium and disodium ($C_{29}H_{43}O_9N_3PNa$ and $C_{29}H_{42}O_9N_3PNa_2$), $N^4$-adamantoyl-1-β-D-arabinofuranosylcytosine-5'-phosphate monosodium and disodium ($C_{20}H_{27}O_9N_3PNa$ and $C_{20}H_{26}O_9N_3PNa_2$).

EXAMPLE 6

Following the procedure of Example 1, the following $N^4$-acyl nucleotides were produced from 1-β-D-arabinofuranosylcytosine 3'-phosphate instead of 1-β-D-arabinofuranosylcytosine-5'-phosphate and the corresponding fatty acid anhydrides:

$N^4$-Myristoyl-1-β-D-arabinofuranosylcytosine-3'-phosphate:

Yield: 76.4%, molecular weight 533 Elementary analysis for $C_{23}H_{40}C_9N_3P$: Calculated: C 51.76%; H 7.50%; N 7.88%. Found: C 51.32%; H 7.68%; N 7.55%.

Ultraviolet absorption spectrum: 249 and 299 mμ

$N^4$-Palmitoyl-1-β-D-arabinofuranosylcytosine-5'-phosphate:

Yield: 81.5%, molecular weight 561. Elementary analysis for $C_{25}H_{44}O_9N_3P$: Calculated: C 53.45%; H 7.84%; N 7.49%. Found: C 53.77%; H 7.90%; N 7.31%.

Ultraviolet absorption spectrum: 248 and 299 mμ

$N^4$-Margaroyl-1-β-D-arabinofuranosylcytosine-3'-phosphate: Yield: 82.6%, molecular weight 575.

Elementary analysis for $C_{26}H_{46}O_9N_3P$: Calculated: C 54.25%; H 8.00%; N 7.26%. Found: C 54.60%; H 8.12%; N 7.19%.

Ultraviolet absorption spectrum: 248 and 299 mμ

$N^4$-Stearoyl-1-β-D-arabinofuranosylcytosine-3'-phosphate: Yield: 81.0% molecular weight 589.

Elementary analysis for $C_{27}H_{48}O_9N_3P$: Calculated: C 54.99%; H 8.21%; N 7.13%. Found: C 55.10%; H 8.27%; N 7.02%.

Ultraviolet absorption spectrum: 248 and 299 mμ

$N^4$-Arachidoyl-1-β-D-arabinofuranosylcytosine-3'-phosphate: Yield: 83.1%, molecular weight 617.

Elementary analysis for $C_{29}H_{52}O_9N_3P$: Calculated: C 56.37%; H 8.43%; N 6.81%. Found: C 56.92%; H 8.51%; N 6.58%.

Ultraviolet absorption spectrum: 248 and 299 mμ.

Furthermore, from 1-β-D-arabinofuranosylcytosine-2'-phosphate and the corresponding fatty acid anhydrides, the following products were produced in the same way as in Example 1:

N[4]-Palmitoyl-1-β-D-arabinofuranosylcytosine-2'-phosphate: Yield: 79.0%, molecular weight 561.

Elementary analysis for $C_{25}H_{44}O_9N_3P$: Calculated: C 53.45%; H 7.84%; N 7.49%. Found: C 53.69%; H 7.93%; N 7.35%.

Ultraviolet absorption spectrum: 249 and 299 mμ

N[4]-Margaroyl-1-β-D-arabinofuranosylcytosine-2'-phosphate: Yield: 80.5%, molecular weight 575.

Elementary analysis for $C_{26}H_{46}O_9N_3P$: Calculated: C 54.23%; H 8.00%; N 7.30%. Found: C 54.71%; H 8.09%; N 7.08%.

Ultraviolet absorption spectrum: 248 and 299 mμ.

N[4]-Stearoyl-1-β-D-arabinofuranosylcytosine-2'-phosphate:

Yield: 81.3%, molecular weight 589. Elementary analysis for $C_{27}H_{48}O_9N_3P$: Calculated: C 54.99%; H 8.21%; N 7.13%. Found: C 55.28%; H 8.29%; N 7.09%.

Ultraviolet absorption spectrum: 248 and 299 mμ

N[4]-Arachidoyl-1-β-D-arabinofuranosylcytosine-2'-phosphate:

Yield: 80.8%, molecular weight 617. Elementary analysis for $C_{29}H_{52}O_9N_3P$: Calculated: C 56.37%; H 8.43%; N 6.81%. Found: C 56.83%; H 8.53%; N 6.60%.

Ultraviolet absorption spectrum: 248 and 299 mμ

EXAMPLE 7

In the same way as in Example 1, the following products were produced from 2'-cytidylic acid or 3'-cytidylic acid, instead of 1-β-D-arabinofuranosylcytosine-3'-phosphate, and the corresponding fatty acid anhydrides instead of stearic anhydride:

N[4]-Margaroylcytidine-2'-phosphate:

Yield: 76.2%, molecular weight 575. Elementary analysis for $C_{26}H_{46}O_9N_3P$: Calculated: C 54.23%; H 8.00%; N 7.30%. Found: C 54.60%; H 8.11%; N 7.13%.

Ultraviolet absorption spectrum: 248 and 299 mμ

N[4]-Stearoylcytidine-2'-phosphate:

Yield: 80.2%, molecular weight 589 Elementary analysis for $C_{27}H_{48}O_9N_3P$: Calculated: C 54.99%; H 8.21%; N 7.13%. Found: C 55.58%; H 8.28%; N 7.05%.

Ultraviolet absorption spectrum: 248 and 299 mμ

N[4]-Arachidoylcytidine-2'-phosphate:

Yield: 83.1%, molecular weight 617. Elementary analysis for $C_{29}H_{52}O_9N_3P$: Calculated: C 56.37%; H 8.43%; N 6.81%. Found: C 56.76%; H 8.59%; N 6.58%.

Ultraviolet absorption spectrum: 249 and 299 mμ

N[4]-Palmitoylcytidine-3'-phosphate:

Yield: 83.5%, molecular weight 561. Elementary analysis for $C_{25}H_{44}O_9N_3P$: Calculated: C 53.45%; H 7.84%; N 7.49%. Found: C 53.71%; H 7.99%; N 7.28%.

Ultraviolet absorption spectrum: 248 and 299 mμ

N[4]-Margaroylcytidine-3'-phosphate:

Yield: 80.8%, molecular weight 575. Elementary analysis for $C_{26}H_{46}O_9N_3P$: Calculated: C 54.23%; H 8.00%; N 7.30%. Found: C 54.44%; H 8.18%; N 7.15%.

Ultraviolet absorption spectrum: 249 and 299 mμ.

N[4]-Stearoylcytidine-3'-phosphate:

Yield: 81.3%, molecular weight 589. Elementary analysis for $C_{27}H_{48}O_9N_3P$: Calculated: C 54.99%; H 8.21%; N 7.13%. Found: C 55.62%; H 8.25%; N 7.01%.

Ultraviolet absorption spectrum: 249 and 200 mμ

N[4]-Arachidoylcytidine-3'-phosphate:

Yield: 84.2%, molecular weight 617. Elementary analysis for $C_{29}H_{52}O_9N_3P$: Calculated: C 56.37%; H 8.43%; N 6.81%. Found: C 56.85%; H 8.49%; N 6.63%.

Ultraviolet absorption spectrum: 248 and 299 mμ.

EXAMPLE 8

Following the same procedure as in Example 1, the following products were produced from 1-β-D-arabinofuranosylcytosine-2',3'-diphosphate or 1-β-D-arabinofuranosylcytosine-3',5'-diphosphate, instead of 1-β-D-arabinofuranosylcytosine-5'-phosphate and corresponding acid anhydrides instead of stearic anhydride. The amount of dioxane used was ⅔'s the amount used in Example 1, however.

N[4]-Palmitoyl-1-β-D-arabinofuranosylcytosine-2',3'-diphosphate:

Yield: 73.5%, molecular weight 641. Elementary analysis for $C_{25}H_{45}O_{12}N_3P_2$: Calculated: C 46.80%; H 7.07%; N 6.55%. Found: C 47.23%; H 7.13%; N 6.34%.

Ultraviolet absorption spectrum: 248 and 299 mμ

N[4]-Margaroyl-1-β-D-arabinofuranosylcytosine-2',3'-diphosphate:

Yield: 76.3%, molecular weight 655. Elementary analysis for $C_{26}H_{47}O_{12}N_3P_2$: Calculated: C 47.63%; H 7.23%; N 6.41%. Found: C 47.91%; H 7.03%; N 6.18%.

Ultraviolet absorption spectrum: 248 and 299 mμ.

N[4]-Stearoyl-1-β-D-arabinofuranosylcytosine-2',3'-diphosphate:

Yield: 77.5%, molecular weight 669. Elementary analysis for $C_{27}H_{49}O_{12}N_3P_2$: Calculated: C 48.42%; H 7.30%; N 6.28%. Found: C 49.68%; H 7.61%; N 6.10%.

Ultraviolet absorption spectrum: 248 and 299 mμ

N[4]-Palmitoyl-1-β-D-arabinofuranosylcytosine-3',5'-diphosphate:

Yield: 78.2%, molecular weight 641. Elementary analysis for $C_{25}H_{45}O_{12}N_3P_2$: Calculated: C 46.80%; H 7.07%; N 6.55%. Found: C 47.42%; H 7.19%; N 6.40%.

Ultraviolet adsorption spectrum: 249 and 299 mμ.

N[4]-Margaroyl-1-β-D-arabinofuranosylcytosine-3',5'-diphosphate:

Yield: 79.1%, molecular wieht 655. Elementary analysis for $C_{26}H_{47}O_{12}N_3P_2$: Calculated: C 47.63%; H 7.23%; N 6.41%. Found: C 47.86%; H 7.32%; N 6.20%.

Ultraviolet adsorption spectrum: 249 and 299 mμ

N[4]-Stearoyl-1-β-D-arabinofuranosylcytosine-3',5'-diphosphate:

Yield: 80.1%, molecular weight 669. Elementary analysis for $C_{27}H_{49}O_{12}N_3P_2$:

Calculated: C 48.42%; H 7.38%; N 6.28%.

Found: C 49.26%; H 7.58%; N 6.09%.

Ultraviolet absorption spectrum: 249 and 299 mμ

N[4]-Arachidoyl-1-β-D-arabinofuranosylcytosine-3',5'-diphosphate:

Yield: 80.8%, molecular weight 697. Elementary analysis for $C_{29}H_{53}O_{12}N_3P_2$: Calculated: C 49.92%; H 7.66%; N 6.02%. Found: C 50.10%; H 7.80%; N 5.94%.

Ultraviolet absorption spectrum: 249 and 299 mμ.

EXAMPLE 9

In the same way as in Example 8, the following products were produced from cytidine-2',5'-diphosphoric acid or cytidine-3',5'-diphosphoric acid, instead of 1-β-D-arabinofuranosylcytosine-2',3'-diphosphoric acid or 1-β-D-arabinofuranosylcytosine-3',5'-diphosphoric acid, and the corresponding fatty acid anhydrides:

N[4]-Palmitoylcytidine-2',5'-diphosphate:

Yield: 77.2%, molecular weight 641. Elementary analysis for $C_{25}H_{45}O_{12}N_3P_2$: Calculated: C 46.80%; H 7.07%; N 6.55%. Found: C 47.39%; H 7.20%; N 6.48%.

Ultraviolet absorption spectrum: 249 and 299 mμ

N[4]-Margaroylcytidine-2',5'-diphosphate:

Yield: 78.2%, molecular weight 655. Elementary analysis for $C_{26}H_{47}O_{12}N_3P_2$: Calculated: C 47.63%; H 7.23%; N 6.41%. Found: C 47.90%; H 7.38%; N 6.30%.

Ultraviolet absorption spectrum: 249 and 299 mμ

$N^4$-Stearoylcytidine-2',5'-diphosphate:

Yield: 80.0%, molecular weight 669. Elementary analysis for $C_{27}H_{49}O_{12}N_3P_2$: Calculated: C 48.42%; H 7.38%; N 6.28%. Found: C 48.83%; H 7.46%; N 6.11%.

$N^4$-Palmitoylcytidine-3',5'-diphosphate:

Yield: 76.8%, molecular weight 641. Elementary analysis for $C_{25}H_{45}O_{12}N_3P_2$: Calculated: C 46.80%; H 7.07%; N 6.55%. Found: C 47.15%; H 7.19%; N 6.41%.

Ultraviolet absorption spectrum: 249 and 299 mμ

$N^4$-Margaroylcytidine-3',5'-diphosphate:

Yield: 81.3%, molecular weight 655. Elementary analysis for $C_{26}H_{47}N_3P_2$: Calculated: C 47.63%; H 7.23%; N 6.41%. Found: C 47.95%; H 7.38%; N 6.22%.

Ultraviolet absorption spectrum: 248 and 299 mμ.

$N^4$-Stearoylcytidine-3',5'-diphosphate:

Yield: 83.1%, molecular weight 669. Elementary analysis for $C_{27}H_{49}O_{12}N_3P_2$: Calculated: C 48.42%; H 7.38%; N 6.28%. Found: C 48.71%; H 7.47%; N 6.09%.

$N^4$-Arachidoylcytidine-3',5'-diphosphate:

Yield: 81.9%, molecular weight 697. Elementary analysis for $C_{29}H_{53}O_{12}N_3P_2$: Calculated: C 49.92%; H 7.66%; N 6.02%. Found: C 50.13%; H 7.79%; N 5.97%.

Ultraviolet absorption spectrum: 249 and 299 mμ.

EXAMPLE 10

20 ml of water, 300 ml of dioxane, and 13.6 g of stearic anhydride were added to 3.0 g of 5-fluoro-1-β-D-arabinofuranosylcytosine and the system reacted for 4 hours at 80° C. After cooling the reaction mixture, water was added thereto and the mixture concentrated to form a precipitate. The precipitate was recovered by filtration, washed with water and dried in a vacuum desiccator. The thus dried precipitate was washed with n-hexane and recrystallized from ethanol to provide 5.7 g of $N^4$-stearoyl-5-fluoro-1-β-D-arabinofuranosylcytosine.

By repeating the same procedure as above using 5-ethylcytidine in place of 5-fluoro-1-β-D-arabinofuranosylcytosine, 5.1 g of $N^4$-stearoyl-5-ethylcytidine was obtained.

0.97 ml of pyridine and then 0.49 ml of methanol were successively added to 10 ml of a dioxane solution of 2.2 ml of phosphorus oxychloride while ice-cooling, and then 3.48 g of $N^4$-stearoyl-5-fluoro-1-β-D-arabinofuranosylcytosine was added to the solution at 0° C followed by stirring for 4 hours, whereby the reaction was completed. The reaction mixture was added with stirring to 100 ml of ice-water containing 6 g of sodium hydrogen carbonate and the precipitate formed was collected by means of a centrifugal separator (3,000 r.p.m.; 15 minutes). To the precipitate thus obtained there was added 100 ml of water and, after stirring the mixture well, the precipitate was collected again by means of a centrifugal separator. This operation was repeated a further 3 times and the precipitate formed collected by filtration and washed with water. The precipitate was dried under a vacuum and recrystallized from methanol to provide 2.90 g of $N^4$-stearoyl-5-fluoro-1-β-D-arabinofuranosylcytosine-5'-phosphate as a white amorphous solid.

Elementary analysis for $C_{27}H_{47}O_9N_3PF$: Calculated: C 53.37%; H 7.80%; N 6.92%. Found: C 53.48%; H 7.82%; N 6.90%.

Ultraviolet absorption spectra (methanol): 248 and 299 mμ.

By following the same procedure as above using $N^4$-stearoyl-5-ethylcytidine in place of $N^4$-stearoyl-5-fluoro-1-β-D-arabinofuranosylcytosine, 2.95 g of $N^4$-stearoyl-5-ethylcytidine-5'-phosphate was obtained.

Elementary analysis for $C_{29}H_{52}O_9N_3P$: Calculated: C 56.38%; H 8.49%; N 6.80%. Found: C 56.41%; H 8.42%; N 6.85%.

Ultraviolet absorption spectra (methanol): 248 and 300 mμ.

5 g of $N^4$-stearoyl-5-fluoro-1-β-D-arabinofuranosylcytosine at 0° C and 15 g of $POCl_3$ were added to 100 ml of cooled pyridine and the mixture stirred for 30 minutes at 0° C to effect reaction. After the reaction was completed, the reaction mixture was added to 500 ml of ice water and the mixture stirred at 0° C for one hour to form crystals. 300 m mole of a cool (5° C) 0.1 normal $NaHCO_3$ solution was then added dropwise to the suspension followed by 600 ml of ethanol. The suspension was stirred for 30 minutes and the precipitate formed collected by centrifugal separation. The precipitate was suspended in 50 ml of water, 50 ml of ethanol was added to the suspension, and the crystals formed were recovered by filtration to provide 2.5 g of powdered $N^4$-stearoyl-5-fluoro-1-β-D-arabinofuranosylcytosine-3',5'-diphosphate.

Elementary analysis for $C_{27}H_{48}O_{12}N_3P_2F$: Calculated: C 47.16%; H 7.04%, N 6.11%. Found: C 47.08%; H 7.05%; N 6.19%.

EXAMPLE 11

20 ml of water was added to 4.0 g of cytidine-5'-pyrophosphate disodium salt and, after further adding 300 ml of dioxane and 13.6 g of stearic anhydride to the mixture, the mixture was heated to 80° C to effect reaction. After cooling the reaction mixture to 5° C, 1 liter of water was added to the reaction mixture, the mixture was concentrated to almost dryness, and 100 ml of ethanol was added to the concentrate to form a precipitate. The precipitate formed was collected by centrifugal separation, suspended in 50 ml of water, and the suspension stirred for 60 minutes. Then, 50 ml of ethanol was added to the suspension and the precipitate thus formed recovered by filtration and washed with ethanol, n-hexane, and then benzene, in this order. The precipitate was dried in a desiccator and recrystallized from water-ethanol (1:1 molar ratio) to provide 1.8 g of powdered $N^4$-stearoylcytidine-5'-pyrophosphate disodium salt. Ultraviolet absorption spectra (water): 248 and 299 mμ.

Following the same procedure as above using myristic anhydride, pentadecanoic anhydride, palmitic anhydride, margaric anhydride, nonadecanoic anhydride, arachidic anhydride, heneicosanic anhydride, behenic anhydride, palmitoleic anhydride, and oleic anhydride, respectively in place of stearic anhydride, the following salts were obtained:

1.7 g of the powder of $N^4$-myristoylcytidine-5'-pyrophosphate disodium salt, 1.7 g of the powder of $N^4$-pentadecanoylcytidine-5'-pyrophosphate disodium salt, 1.5 g of the powder of $N^4$-palmitoylcytidine-5'-pyrophosphate disodium salt, 1.4 g of the powder of $N^4$-margaroylcytidine-5'-pyrophosphate disodium salt.

1.8 g of the powder of $N^4$-nonadecanoylcytidine-5'-pyrophosphate disodium salt, 1.7 g of the powder of $N^4$-arachidoyl-5'-pyrophosphate disodium salt, 1.8 g of the powder of $N^4$-heneicosanoylcytidine-5'-pyrophosphate disodium salt, 2.1 g of the powder of $N^4$-behenoylcytidine-5'-pyrophosphate disodium salt, 1.5 g of the powder of $N^4$-palmitoleoylcytidine-5'-pyrophosphate disodium salt, and 1.7 g of the powder of $N^4$-oleoylcytidine-5'-pyrophosphate disodium salt.

EXAMPLE 12

Following the same procedure as in Example 11 except using 4.8 g of cytidine-5'-triphosphate trisodium salt in place of 4.0 g of cytidine-5'-pyrophosphate disodium salt, 2.1 g of $N^4$-stearoylcytidine-5'-triphosphate trisodium salt was obtained.

Upon adding 3 moles of hydrochloric acid per one mole of the above-described sodium salt (same as the sodium salts shown in Example 11), the sodium salt was converted into the acid form.

EXAMPLE 13

0.97 ml of pyridine and 0.49 ml of methanol were successively added under ice cooling conditions to 10 ml of a dioxane solution of 2.20 ml of phosphorus oxychloride and then 3.30 g of $N^4$-stearoyl-1-$\beta$-D-arabinofuranosylcytosine was added to the solution at the same temperature. The mixture was stirred for 4 hours to complete the reaction. The reaction mixture was added to 100 ml of ice water containing 6 g of sodium hydrogen carbonate with stirring, and the precipitate formed collected by centrifugal separation (3,000 r.p.m.; 15 minutes). The precipitate was added to 100 ml of water, the mixture was stirred, and the precipitate again collected by centrifugal separation. These operations were repeated 3 further times and the precipitate obtained collected by filtration, washed with water, and dried in a vacuum. The solid residue was then recrystallized from methanol to provide 3.01 g of $N^4$-stearoyl-1-$\beta$-D-arabinofuranosylcytosine-5'-phosphate as a white amorphous solid.

Elementary analysis for $C_{27}H_{48}O_9N_3P$: Calculated: C 54.99%; H 8.21%; N 7.13%. Found: C 54.16%; H 8.42%; N 7.08%.

Ultraviolet absorption spectrum (methanol): $\lambda_{max}$: 248 m$\mu$ (1.5 × 10$^4$) and 299 m$\mu$ (8.0 × 10$^2$), Melting point: 215°–218° C (decomp.):

By adding a part (50 mg) of the product to 5 ml of aqueous ammonia and 10 ml of methanol, heating the mixture for 3 hours at 60° C, and concentrating and drying the product, 1-$\beta$-D-arabinofuranosylcytosine-5'-phosphate (confirmed by thin layer chromatography and nuclear magnetic resonance spectrum) was obtained.

1.10 g of $N^4$-stearoyl-1-$\beta$-D-arabinofuranosylcytosine-5'-phosphate was suspended in a mixed solvent of 50 ml of water and 50 ml of ethanol and, after adding thereto 0.168 g of sodium hydrogen carbonate, the mixture was vigorously stirred, whereby sodium hydrogen carbonate disappeared to provide a homogeneous colloidal solution. By lyophilizing the mixture, 1.14 g of $N^4$-stearoyl-1-$\beta$-D-arabinofuranosylcytosine-5'-phosphate monosodium salt was obtained as a white solid.

The compound of this invention may be obtained as the alkali metal salt thereof merely by using water in place of water and methanol in the above procedure, for example, 1.10 g of $N^4$-stearoyl-1-$\beta$-D-arabinofuranosylcytosine-5'-phosphate was suspended in 200 ml of water, and, after adding 0.16 g of sodium hydrogen carbonate to the suspension, the mixture was stirred for 30 minutes at 60° C to provide a solution. The solution was filtered and then subjected to lyophilization to provide 118 g $N^4$-stearoyl-1-$\beta$-D-arabinofuranosylcytosine-5'-phosphate monosodium salt as a white solid.

Elementary analysis for $C_{27}H_{47}O_9N_3PNa$: Calculated: C 52.93%; H 7.73%; N 6.86%. Found: C 52.24%; H 7.56%; N 6.33%.

Ultraviolet absorption spectra (water): 247 and 299 m$\mu$

Instead of using 0.168 g of sodium hydrogen carbonate, 0.487 g of a 50% aqueous solution of choline and 0.122 g of ethanolamine were each used to obtain 1.2 g of $N^4$-stearoyl-1-$\beta$-D-arabinofuranosylcytosine monocholine and 1.15 g of the ethanolamine salt thereof, respectively.

Similarly, 1.10 g of $N^4$-stearoyl-1-$\beta$-D-arabinofuranosylcytosine-5'-phosphate was suspended in a mixed solvent of 70 ml of water and 35 ml of ethanol and, after adding thereto 0.336 g of sodium hydrogen carbonate, the mixture was vigorously stirred at 50° C for 3 hours, whereby sodium hydrogen carbonate disappeared to yield a homogeneous colloidal solution. By lyophilizing the solution, 1.18 g of $N^4$-stearoyl-1-$\beta$-D-arabinofuranosylcytosine-5'-phosphate disodium salt was obtained as a white solid.

Elementary Analysis for $C_{27}H_{46}O_9N_3PNa_2$: Calculated: C 51.18%; H 7.32%; N 6.63%. Found: C 51.29%; H 7.11%; N 6.40%.

Ultraviolet absorption spectra (water):
$\lambda_{max}$: 246 m$\mu$ and 299 m$\mu$

EXAMPLE 14

By the same procedure as in Example 13, the following 5'-phosphates were produced by using $N^4$-acyl-1-$\beta$-D-arabinofuranosylcytosine instead of $N^4$-stearoyl-1-$\beta$-D-arabinofuranosylcytosine.

$N^4$-Palmitoyl-1-$\beta$-D-arabinofuranosylcytosine-5'-phosphate:

Elementary analysis for $C_{25}H_{44}O_9N_3P$: Calculated: C 53.46%; H 7.90%; N 7.48%. Found: C 53.22%; H 7.99%; N 7.39%.

Ultraviolet absorption spectra (methanol):
$\lambda_{max}$: 248 m$\mu$ and 299 m$\mu$ $N^4$-Margaroyl-1-$\beta$-D-arabinofuranosylcytosine-5'-phosphate:

Elementary analysis for $C_{26}H_{46}O_9N_3P$: Calculated: C 54.25%; H 8.06%; N 7.30%. Found: C 54.01%; H 8.11%; N 7.18%.

Ultraviolet absorption spectra (methanol):
$\lambda_{max}$: 248 m$\mu$ and 299 m$\mu$ $N^4$-Montanoyl-1-$\beta$-D-arabinofuranosylcytosine-5'-phosphate:

Elementary analysis for $C_{37}H_{68}O_9N_3P$: Calculated: C 60.88%; H 9.39%; N 5.76%. Found: C 60.61%; H 9.44%; N 5.64%.

Ultraviolet absorption spectra (methanol):
$\lambda_{max}$: 248 m$\mu$ and 299 m$\mu$ $N^4$-oleoyl-1-$\beta$-D-arabinofuranosylcytosine-5'-phosphate:

Elementary analysis for $C_{27}H_{46}O_9N_3P$: Calculated: C 55.18%; H 7.89%; N 7.15%. Found: C 54.93%; H 7.94%; N 7.12%.

Ultraviolet absorption spectra (methanol):
$\lambda_{max}$: 248 m$\mu$ and 299 m$\mu$ $N^4$-Admantoyl-1-$\beta$-D-arabinofuranosylcytosine-5'-phosphate:

Elementary analysis for $C_{20}H_{28}O_9N_3P$: Calculated: C 49.48%; H 5.81%; N 8.66%. Found: C 49.29%; H 5.87%; N 8.53%.

Ultraviolet absorption spectra (methanol):
$\lambda_{max}$: 248 m$\mu$ and 301 m$\mu$ In a manner similar to the above procedure, other $N^4$-higher acyl-1-$\beta$-D-arabinofuranosylcytosine-5'-phosphates were produced by using other $N^4$-aryl-1-$\beta$-D-arabinofuranosylcytosines instead of $N^4$-palmitoyl-1-$\beta$-D-arabinofuranosylcytosine. They were as follows:

$N^4$-Myristoyl-1-$\beta$-D-arabinofuranosylcytosine-5'-phosphate, $N^4$-pentadecanoyl-1-$\beta$-D-arabinofuranosylcytosine-5'-phosphate, $N^4$-nonadecanoyl-1-$\beta$-D-arabinofuranosylcytosine-5'-phosphate, $N^4$-arachidoyl-1-$\beta$-D-arabinofuranosylcytosine-5'-phosphate, $N^4$-heneicosanoyl-1-$\beta$-D-arabinofuranosylcytosine-5'-phosphate, $N^4$-behenoyl-1-$\beta$-D-arabinofuranosylcytosine-5'-phosphate, $N^4$-tricosanoyl-1-$\beta$-D-arabinofuranosylcytosine-5'-phosphate, $N^4$-lignoceroyl-1-$\beta$-D-arabinofuranosylcytosine-5'-phosphate, $N^4$-cerotoyl-1-$\beta$-D-arabinofuranosylcytosine-5'-phosphate, $N^4$-elaidoyl-1-$\beta$-D-arabinofuranosylcytosine-5'-phosphate, $N^4$-linoleoyl-1-$\beta$-D-arabinofuranosylcytosine-5'-phosphate, $N^4$-linolenoyl-1-$\beta$-D-arabinofuranosylcytosine-5'-phosphate, $N^4$-palmitoleoyl-1-$\beta$-D-arabinofuranosylcytosine-5'-phosphate, $N^4$-arachidonoyl-1-$\beta$-D-arabinofuranosylcytosine-5'-phosphate.

EXAMPLE 15

1.8 g of $N^4$-stearoyl-1-$\beta$-D-arabinofuranosylcytosine was added to a mixed solvent of 10 ml of dioxane, 1.0 ml of phosphorus oxychloride, and 0.112 ml of water, and the mixture stirred for 6 hours at room temperature to effect reaction. After the reaction was completed, the reaction mixture was dropwise added to 20 ml of ice-water to form crystals. The suspension was adjusted to pH 2 with sodium hydrogen carbonate and then the crystals collected by means centrifugal separation (3 × 10³ r.p.m.; 15 minutes). By drying the crystals in desicator under reduced pressure (0.5 atmospheric pressure), 1.3 g of powdered $N^4$-stearoyl-1-$\beta$-D-arabinofuranosylcytosine-5'-phosphate was obtained.

EXAMPLE 16

0.69 ml of phosphorus oxychloride was added to 4.5 ml of triethyl phosphate and the mixture was cooled to 0° C. After adding thereto 0.045 ml of water and 1.273 g of $N^4$-stearoyl-1-$\beta$-D-arabinofuranosylcytosine, the mixture was stirred for 4 hours at room temperature and then for 2 hours at 80° C to effect reaction. After the reaction was completed, the reaction mixture was treated as in Example 14 to provide 1.1 g of powdered $N^4$-stearoyl-1-$\beta$-D-arabinofuranosylcytosine-5'-phosphate.

EXAMPLE 17

0.67 g of $N^4$-stearoyl-1-$\beta$-D-arabinofuranosylcytosine was suspended in 2.5 ml of ethyl acetate and the supension cooled to 0° C. After adding to the suspension 12.5 ml of phosphorus oxychloride, the mixture was stirred for 2 hours at room temperature and then for 2 hours at 50° C to effect reaction. After the reaction was completed, the reaction mixture was treated as in Example 14 to provide 0.42 g of powdered $N^4$-stearoyl-1-$\beta$-D-arabinofuranosylcytosine-5'-phosphate.

EXAMPLE 18

10 ml of $N^4$-stearoyl-1-$\beta$-D-arabinofuranosylcytosine and 100 m mole of phosphorus oxychloride were added to 100 ml of pyridine under ice-cooling conditions and the mixture stirred for 30 minutes at 0° C to effect reaction. After the reaction was completed, the reaction mixture was added to 500 ml of ice water and the mixture stirred for one hour to form crystals. Then, 300 m moles of a 0.1 normal $NaHCO_3$ solution cooled was added to the suspension, whereafter 600 ml of ethanol was added to the solution followed by stirring for 30 minutes and the crystals which formed was recovered by centrifugal separation. 9 g of the crystals were suspended in 50 ml of water and the suspension stirred for 60 minutes. Then, 50 ml of ethanol was added to the suspension and the crystals recovered by filtration to provide 2.3 g of powdered $N^4$-stearoyl-1-$\beta$-D-arabinofuranosylcytosine-3',5'-diphosphate.

Elementary analysis for $C_{27}H_{49}O_{12}N_3P_2$: Calculated: C 48.42%; H 7.38%; N 6.28%; P 9.24%. Found: C 48.43%; H 7.92%; N 6.11%; P 9.20%.

Ultraviolet absorption spectra (water):
$\lambda_{max}$: 248 m$\mu$ and 299 m$\mu$ When 5 ml of concentrated aqueous ammonia and 10 ml of methanol were added to 50 mg of the reaction product and the mixture heated at 60° C for 3 hours, concentrated and dried, the dried product was analyzed by paper electrophoresis to determine the position of the phosphate of the dried product. That is, the product was put on a certain point of the paper (called the zero point or original point). 1-$\beta$-D-arabinofuranosylcytosine-5'-phosphate and 1-$\beta$-D-arabinofuranosylcytosine-3',5'-diphosphate were also put on the zero point of other papers, separately. Then, the three papers were put on an electrophorator. After electrophoresis, the mobility of the 3 materials was checked by ultraviolet absorption spectra. The mobility of the dried product was the same as that of 1-$\beta$-D-arabinofuranosylcytosine-3',5'-diphosphate, but not the same as that of 1-$\beta$-D-arabinofuranosylcytosine-5-phosphate. The result indicates that the dried product can be 1-$\beta$-D-arabinofuranosylcytosine-3',5'-diphosphate, but not 1-$\beta$-D-arabinofuranosyloytosine-5'-phosphate, and that the product before hydrolysis by ammoniamethanol can be $N^4$-stearoyl-1-$\beta$-D-arabinofuranosylcytosine-3',5'-diphosphate, but not $N^4$-stearoyl-1-$\beta$-D-arabinofuranosylcytosine-5'-phosphate.

EXAMPLE 19

5 m moles of $N^4$-palmitoyl-1-$\beta$-D-arabinofuranosylcytosine and 50 m moles of phosphorus oxychloride were added to 25 ml of pyridine under ice-cooling conditions and the mixture stirred for 20 minutes under ice-cooling conditions. After the reaction was completed, the reaction mixture was added to 250 ml of ice-water and the mixture stirred for one hour to form crystals. To the resulting suspension was dropwise added 150 m moles of a cooled (5° C) 0.1 normal sodium hydroxide solution and, after further adding 300 ml of ethanol, the mixture was stirred for 30 minutes. By subjecting the mixture to centrifugal separation, 3.0 g of crude crystals were obtained. The crystals were dissolved in 15 ml of water and the solution stirred for 60 minutes. Then, after adding 50 ml of ethanol to the solution followed by stirring, the crystals formed were collected by centrifugal separation and dried in a desiccator under a reduced pressure (0.5 atmospheric pressure) to provide 1.7 g of white powdered $N^4$-palmitoyl-$\beta$-D-arabinofuranosylcytosine-3',5'-diphosphate sodium salt.

By following the same procedure as above using $N^4$-myristoyl-1-$\beta$-D-arabinofuranosylcytosine, $N^4$-lauroyl-1-$\beta$-D-arabinofuranosylcytosine, $N^4$-myristoylcytidine, $N^4$-lauroylcytidine and $N^4$-palmitoylcytidine, respectively in place of $N^4$-palmitoyl-1-$\beta$-D-arabinofuranosylcytosine, the following products were obtained:

$N^4$-myristoyl-1-$\beta$-D-arabinofuranosylcytosine-3',5'-diphosphate sodium salt (1.0 g), $N^4$-lauroyl-1-$\beta$-D-arabinofuranosylcytosine-3',5'-diphosphate sodium salt (1.8 g), $N^4$-myristoylcytidine-3',5'-diphosphate sodium salt (1.0 g), $N^4$-lauroylcytidine-3',5'-diphosphate sodium salt (1.7 g), $N^4$-palmitoylcytidine-3',5'-diphosphate sodium salt (1.7 g).

As a result of analyzing the compounds thus obtained after deacylation, it was confirmed that the 3'-position and 5'-position of the compounds had been phosphated.

EXAMPLE 20

12.5 m moles of $SOCl_2$, 0.135 ml of water, 15 m moles of pyridine and 2.5 m moles of $N^4$-myristoylcytidine-5'-phosphate were added to 5 ml of dioxane under ice-cooling conditions and the mixture stirred for 5 hours at room temperature to dissolve the raw materials and effect reaction. After the reaction was completed, the reaction mixture was added to 50 ml of ice-water to form white crystals. The crystals were recovered by filtration and dried in a desiccator to provide 800 mg of $N^4$-myristoylcytidine-2',3'-sulfinyl-5'-phosphate having the absorptions specific to the sulfinyl moiety at 1200 $cm^{-1}$ and 1020 $cm^{-1}$.

By dissolving 0.2 ml of $N^4$-myristoylcytidine-2',3'-sulfinyl-5'-phosphate in 10 ml of N,N-dimethylformamide and heating the solution for 5 hours at 100° C, 1.1 g of $N^4$-myristoyl-1-$\beta$-D-arabinofuranosylcytosine-5'-phosphate was obtained.

By following the above procedure using $N^4$-pentadecanoylcytidine-5'-phosphate, $N^4$-palmitoylcytidine-5'-phosphate, $N^4$-margaroylcytidine-5'-phosphate, $N^4$-stearoylcytidine-5'-phosphate, $N^4$-nonadecanoylcytidine-5'-phosphate, $N^4$-arachidoylcytidine-5'-phosphate, $N^4$-heneicosanoylcytidine-5'-phosphate, and $N^4$-behenoylcytidine-5'-phosphate, respectively, instead of $N^4$-myristoylcytidine-5'-phosphate, the following products were obtained;

$N^4$-pentadecanoyl-1-$\beta$-D-arabinofuranosylcytosine-5'-phosphate, $N^4$-palmitoyl-1-$\beta$-D-arabinofuranosylcytosine-5'-phosphate, $N^4$-margaroyl-1-$\beta$-D-arabinofuranosylcytosine-5'-phosphate, $N^4$-stearoyl-1-$\beta$-D-arabinofuranosylcytosine-5'-phosphate, $N^4$-nonadecanoyl-1-$\beta$-D-arabinofuranosylcytosine-5'-phosphate, $N^4$-arachinodoyl-1-$\beta$-D-arabinofuranosylcytosine-5'-phosphate, $N^4$-heneicosanoyl-1-$\beta$-D-arabinofuranosylcytosine-5'-phosphate, and $N^4$-behenoyl-1-$\beta$-D-arabinofuranosylcytosine-5'-phosphate.

Also, the following the above procedure using $N^4$-myristoylcytidine-5'-pyrophosphate, $N^4$-pentadecanoylcytidine-5'-pyrophosphate, $N^4$-palmitoylcytidine-5'-pyrophosphate, $N^4$-margaroylcytidine-5'-pyrophosphate, $N^4$-stearoylcytidine-5'-pyrophosphate, $N^4$-nonadecanoylcytidine-5'-pyrophosphate, $N^4$-arachidoylcytidine-5'-pyrophosphate, $N^4$-heneicosanoylcytidine-5'-pyrophosphate, $N^4$-behenoylcytidine-5'-pyrophosphate, and $N^4$-oleoylcytidine-5'-pyrophosphate, respectively, instead of $N^4$-myristoylcytidine-5'-phosphate, the following products were obtained:

$N^4$-myristoyl-1-$\beta$-D-arabinofuranosylcytosine-5'-pyrophosphate, $N^4$-pentadecanoyl-1-$\beta$-D-arabinofuranosylcytosine-5'-phosphate, $N^4$-palmitoyl-1-$\beta$-D-arabinofuranosylcytosine-5'-pyrophosphate, $N^4$-margaroyl-1-$\beta$-D-arabinofuranosylcytosine-5'-pyrophosphate, $N^4$-stearoyl-1-$\beta$-D-arabinofuranosylcytosine-5'-pyrophosphate, $N^4$-nonadecanoyl-1-$\beta$-D-arabinofuranosylcytosine-5'-pyrophosphate, $N^4$-arachidoyl-1-$\beta$-D-arabinofuranosylcytosine-5'-pyrophosphate, $N^4$-heneicosanoyl-1-$\beta$-D-arabinofuranosylcytosine-5'-pyrophosphate, $N^4$-behenoyl-1-$\beta$-D-arabinofuranosylcytosine-5'-pyrophosphate, and $N^4$-oleoyl-1-$\beta$-D-arabinofuranosylcytosine-5'-pyrophosphate.

Similarly, $N^4$-stearoyl-1-$\beta$-D-arabinofuranosylcytosine-5'-triphosphate was obtained using $N^4$-stearoylcytidine-5'-triphosphate.

EXAMPLE 21

10 m moles of $N^4$-stearoyl-1-$\beta$-D-arabinofuranosylcytosine and 100 m moles of phosphorus oxychloride were added to 100 ml of pyridine under ice-cooling conditions and the mixture stirred for 10 minutes at 0° C to effect reaction. After the reaction was completed, the reaction mixture was added to 500 ml of ice-water and the mixture stirred for one hour to form crystals. To the reaction suspension there was dropwise added 300 m moles of a 0.1 normal cooled (5° C) $NaHCO_3$ solution. After further adding 600 ml of ethanol to the suspension followed by stirring for 30 minutes at 5° C, the crystals formed were collected by centrifugal separation (9.8 g). Then, 9 g of the crystals were suspended in 50 ml of water and, after adding thereto 50 ml of ethanol, the crystals formed were recovered by filtration to provide 2.3 g of powdered $N^4$-stearoyl-1-$\beta$-D-arabinofuranosylcytosine-3',5'-diphosphate.

Elementary analysis for $C_{27}H_{49}O_{12}N_3P_2$: Calculated: C 48.42%; H 7.38%; N 6.28%; P 9.24%. Found: C 48.43%, H 7.9%; N 6.11%; P 9.20%.

Ultraviolet absorption spectra (water):
$\lambda_{max}$: 248 m$\mu$ and 299 m$\mu$

EXAMPLE 22

5 m moles of $N^4$-palmitoyl-1-$\beta$-D-arabinoylfuranosylcytosine and 50 m moles of phosphorus oxychloride were added to 25 ml of pyridine under ice-cooling conditions and the mixture stirred for 20 minutes under ice-cooling conditions. After the reaction was completed, the reaction mixture was added to 250 ml of ice-water followed by stirring for one hour to form crystals. To the suspension was dropwise added 150 m moles of a cooled 0.1 normal solution of NaHCO$_3$ and, after further adding thereto 300 ml of ethanol, the mixture was stirred at 5° C for 30 minutes. The mixture was subjected to centrifugal separation to provide 3.0 g of crystals. The crystals were dissolved in 15 ml of water followed by stirring at 25° C for 60 minutes. Then, 50 ml of ethanol was added to the solution followed by stirring and the mixture was subjected to centrifugal separation to provide 1.7 g of white powdered N$^4$-palmitoyl-1-β-D-arabinofuranosylcytosine-3',5'-diphosphate.

EXAMPLE 23

Solubility test:

In the aforesaid examples, the products were obtained as white solids.

The mono-alkali metal salt and di-alkali metal salt of N$^4$-acyl-1-β-D-arabinofuranosylcytosine-5'-phosphate of this invention possessed increased solubility in water as compared with the starting material, N$^4$-acyl-1-β-D-arabinofurasylcytosine, as illustrated in the following table.

Table 1

| | (Solubility in water) | | |
|---|---|---|---|
| | N$^4$-acyl-Ara-C | N$^4$-acyl-5'-PNa | N$^4$-acyl-5'-PNa$_2$ |
| N$^4$-Stearoyl | <0.01 mg/ml | >10 mg/ml | > 50 mg/ml |
| N$^4$-Palmitoyl | 0.01 mg/ml | >30 mg/ml | >150 mg/ml |
| N$^4$-Margaroyl | <0.01 mg/ml | >10 mg/ml | > 50 mg/ml |
| N$^4$-Montanoyl | <0.01 mg/ml | 1 mg/ml | > 5 mg/ml |
| N$^4$-Oleoyl | 0.05 mg/ml | >50 mg/ml | >250 mg/ml |
| N$^4$-Adamantoyl | 0.01 mg/ml | 2 mg/ml | > 10 mg/ml |

In Table 1, -Ara-C means "-1-β-D-arabinofuranosylcytosine" and -5'-Pna and -5'-PNa$_2$ mean "-1-β-D-arabinofuranosylcytosine-5'-phosphate monosodium salt" and "-1-β-D-arabinofuranosylcytosine-5'-phosphate disodium salt," respectively.

As is shown in the above table, the phosphoric acid esters of the montanoyl derivative and adamantoyl derivative are inferior to the phosphoric acid esters of the derivatives of acyls having 14–22 carbon atoms with respect to their solubility in water.

The solubility in water of the 2'-phosphates and the 3'-phosphates is almost the same as that of the 5'-phosphates. Also, the water solubility of the 3',5'-diphosphates, the 5'-pyrophosphates, and the 5'-triphosphates is higher than that of the 5'-phosphates.

EXAMPLE 24

Biological test:

To test the antitumour activity for mice of the novel compounds, the N$^4$-acyl-1-β-D-arabinofuranosylcytosine-phosphate monosodium salts of this invention, 100,000 cells/mouse of leukemia L-1210 were administered by intraperitoneal injection to groups of CDF-1 male mice (one group-three mice) and, directly after injection, after 2 days, and after 6 days, a physiological saline solution containing the test material in an amount of 100, 200, or 400 mg/kg. was administered by intraperitoneal injection to the mice. Further, a physiological saline solution containing no test material was similarly administered to the mice infected with L-1210 for comparison purposes.

The antitumour activity for mice of the test material was evaluated by means of survival rate comparison, T/C (%), that is, 100 times the mean survival period of the groups injected with the test material divided by the mean survival period of the comparison groups which were not injected with the test material.

Further, for comparison, the following materials were also subjected to the same biological test:

1-β-D-Arabinofuranosylcytosine.

1-β-D-Arabinofuranosylcytosine-5'-phosphate.

N$^4$-Lower acyl-1-β-D-arabinofuranosylcytosine (wherein the lower acyl group is the acyl group derived from a straight chain fatty acid having 2–12 carbon atoms).

N$^4$-Lower acyl-1-β-D-arabinofuranosylcytosine-5'-phosphate monosodium salt (wherein the lower acyl group is the acyl group derived from a straight chain fatty acid having 2–12 carbon atoms).

N$^4$-higher acyl-1-β-D-arabinofuranosylcytosine (wherein the higher acyl is the acyl group derived from a straight chain fatty acid having at least 14 carbon atoms).

The results are shown in the following Table.

Table 2

| | N$^4$-acyl-Ara-C | | | N$^4$-acyl-5'-PNa | | |
|---|---|---|---|---|---|---|
| | T/C (%) | | | T/C (%) | | |
| R (N$^4$-acyl group) | 100 (mg/kg) | 200 (mg/kg) | 400 (mg/kg) | 100 (mg/kg) | 200 (mg/kg) | 400 (mg/kg) |
| Lower acyl: | | | | | | |
| Acetyl | 125 | 125 | 125 | 101 | 99 | 99 |
| Propionyl | 131 | 131 | 135 | 99 | 100 | 101 |
| Butyryl | 131 | 131 | 139 | 105 | 102 | 100 |
| Valeryl | 133 | 171 | 191 | 101 | 99 | 101 |
| Caproyl | 125 | 133 | 150 | 103 | 105 | 101 |
| Caprylyl | 123 | 127 | 163 | 103 | 101 | 99 |
| Capryl | 159 | 188 | >284 | 103 | 102 | 98 |
| Lauroyl | 177 | 272 | >296 | 110 | 115 | 115 |
| Higher acyl: | | | | | | |
| Myristoyl | 206 | 127 | 90 | >219 | >261 | 93 |
| Pentadecanoyl | 302 | 287 | 91 | >302 | >287 | 86 |
| Palmitoyl | >346 | 83 | 78 | >349 | >342 | 98 |
| Margaroyl | >397 | 188 | 99 | >395 | >382 | 101 |
| Stearoyl | >274 | 123 | 111 | >363 | >338 | 104 |
| Nonadecanoyl | 382 | 216 | 134 | 385 | 232 | 102 |
| Arachidoyl | 313 | 128 | 105 | 320 | 130 | 106 |
| Behenoyl | 313 | 260 | 256 | 316 | 280 | 270 |
| Oleoyl | 261 | 135 | 94 | 270 | 156 | 103 |
| Linoleoyl | 268 | 140 | 112 | 275 | 145 | 120 |
| Arachidonoyl | 269 | 137 | 114 | 274 | 148 | 115 |
| Ara-C | 127 | 136 | 164 | — | — | — |
| Ara-C-5'-(P) | — | — | — | 119 | 131 | 143 |

Table 2-continued

| Kind of $N^4$-acyl-Ara-C-phosphate | T/C (%) | | |
|---|---|---|---|
| | 100 (mg/kg) | 200 (mg/kg) | 400 (mg/kg) |
| $N^4$-stearoyl-Ara-C-2'-PNa | 228 | 146 | 121 |
| $N^4$-stearoyl-Ara-C-3'-PNa | 286 | 219 | 112 |
| $N^4$-stearoyl-Ara-C-2',3'-(PNa)$_2$ | 184 | 119 | 103 |
| $N^4$-stearoyl-Ara-C-3',5'-(PNa)$_2$ | 215 | 138 | 107 |

In Table 2, R means the $N^4$-acyl group, Ara-C means 1-$\beta$-D-arabinofuranosylcytosine, and Ara-C-5'- (P) means 1-$\beta$-D-arabinofuranosylcytosine-5'-phosphate. Furthermore, $N^4$-acyl-Ara-C means $N^4$-acyl-1-$\beta$-D-arabinofuranosylcytosine and $N^4$-acyl-Ara-C-5'-PNa means $N^4$-acyl-1-$\beta$-D-arabinofuranosylcytosine-5'-phosphate monosodium salt and $N^4$-stearoyl-Ara-C-2'-PNa means $N^4$-stearoyl-1-$\beta$-D-arabinofuranosylcytosine-2'-phosphate monosodium salt.

From the results shown in the above table, the following conclusions can be reached.

(1) The materials of this invention, $N^4$-higher acyl-1-$\beta$-D-arabinofuranosylcytosine-5'-phosphate monosodium salts (wherein the higher acyl is the acyl group derived from a straight chain fatty acid having at least 14 carbon atoms) possess an antileukemial effect on mice the same as or superior to the corresponding $N^4$-higher acyl-1-$\beta$-D-arabinofuranosylcytosines.

(2) As described in the specification of Japanese Pat. Application No. 59709/1973, the $N^4$-lower acyl-1-$\beta$-D-arabinofuranosylcytosines are inferior to the $N^4$-higher acyl-1-$\beta$-D-arabinofuranosylcytosines in antileukemial effect or mice, but the $N^4$-lower acyl-1-$\beta$-D-arabinofuranosylcytosine-5'-phosphate monosodium salts, which are the 5'-phosphate derivatives of the $N^4$-lower acyl-1-$\beta$-D-arabinofuranosylcytosines, are more inferior to the corresponding $N^4$-lower acyl 1-$\beta$-D-arabinofuranosylcytosines in antileukemial effect.

(3) 1-$\beta$-D-arabinofuranosylcytosine-5'-phosphate was inferior to 1-$\beta$-D-arabinofuranosylcytosine in antileukemical effect on mice.

(4) Among the $N^4$-stearoyl-1-$\beta$-D-arabinofuranosylcytosine phosphate derivatives, $N^4$-stearoyl-1-$\beta$-D-arabinofuranosylcytosine-5'-phosphate had the highest antileukemial effect on mice.

The excellent antileukemial effect on mice of the $N^4$-higher acyl-1-$\beta$-D-arabinofuranosylcytosine-phosphates, in particular the $N^4$-higher acyl-1-$\beta$-D-arabinofuranosylcytosine-5'-phosphates, was quite unexpected.

As described above, the inventors have succeeded in obtainining water-soluble derivatives of $N^4$-higher acyl-1-$\beta$-D-arabinofuranosylcytosines showing an excellent antileukemial effect on leukemia L-1210.

While the invention has been described in detail and with reference to specific embodiments thereof, it will be apparent to one skilled in the art that various changes and modifications can be made therein without departing from the spirit and scope thereof.

We claim:

1. A nucleotide derivative represented by the general formula

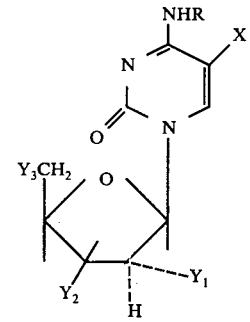

wherein R represents an acyl group having 14 to 22 carbon atoms and having an aliphatic acyl moiety; X represents a hydrogen atom, a halogen atom, an alkyl group having 1 to 4 carbon atoms, or a trifluoromethyl group; and one of $Y_1$ and $Y_3$, or both $Y_1$ and $Y_3$, or both $Y_2$ and $Y_3$ in case of ribosyl; and one of $Y_1$ and $Y_3$, or both $Y_1$ and $Y_2$ or both $Y_2$ and $Y_3$ in case of arabinosyl, represent a phosphate, a pyrophosphate, a triphosphate, or a salt thereof, the balance of $Y_1$, $Y_2$ and $Y_3$ representing a hydroxyl group, wherein said salt is a pharmaceutically acceptable salt.

2. The nucleotide derivative as claimed in claim 1, wherein said pharmaceutically acceptable salt is a pharmaceutically acceptable alkaline or alkaline earth metal salt, pharmaceutically acceptable ammonium salt or a pharmaceutically acceptable amine salt.

3. The nucleotide derivative as claimed in claim 2, wherein said pharmaceutically acceptable alkaline or alkaline earth metal salt is a sodium salt, a potassium salt, a calcium salt or an aluminum salt; said pharmaceutically acceptable ammonium salt is an ammonium salt; and said pharmaceutically acceptable amine salt is a trialkylamine, procaine, dibenzylamine, N-benzyl-$\beta$-phenethylamine, N,N'-dibenzylethylene diamine, dehydrobiethylamine, an N-lower alkyl piperidine, arginine, lysine or choline.

4. The nucleotide derivative as claimed in claim 1, wherein said furanosyl is arabinofuranosyl.

5. The nucleotide derivative as claimed in claim 4, wherein X is a hydrogen atom.

6. The nucleotide derivative as claimed in claim 5, wherein said acyl group (R) is a straight chain fatty acid acyl group having 14 to 22 carbon atoms.

7. The nucleotide derivative as claimed in claim 6, wherein said acyl group is a myristoyl group, a pentadecanoyl group, a palmitoyl group, a margaroyl group, a stearoyl group, a nonadecanoyl group, an arachidoyl group, a heneicosanoyl group or a behenoyl group.

8. The nucleotide derivative as claimed in claim 7, wherein said acyl group is a stearoyl group.

9. The nucleotide derivative as claimed in claim 7, wherein at least one of $Y_1$ and $Y_3$ is a phosphate or a pharmaceutically acceptable salt thereof.

10. The nucleotide derivative as claimed in claim 7, wherein said derivative is an $N^4$-acyl-1-β-D-arabinofuranosylcytosine-5'-phosphate, an $N^4$-acyl-1-β-D-arabinofuranosylcytosine-3',5'-diphosphate or a pharmaceutically acceptable salt thereof.

11. The nucleotide derivative as claimed in claim 1, wherein said derivative is an $N^4$-acyl-1-β-D-arabinofuranosylcytosine-5'-phosphate or a pharmaceutically acceptable salt thereof.

12. The nucleotide derivative as claimed in claim 1, wherein said derivative is an $N^4$-acyl-1-β-D-arabinofuranosylcytosine-3',5'-diphosphate or a pharmaceutically acceptable salt thereof.

13. The nucleotide derivative as claimed in claim 1, wherein said acyl group (R) is a myristoyl group, a pentadecanoyl group, a palmitoyl group, a margaroyl group, a stearoyl group, a nonadecanoyl group, an arachidoyl group, a heneicosanoyl group, or a behenoyl group, and said furabosyl is ribofuranosyl.

14. The nucleotide derivative as claimed in claim 1, wherein one of $Y_1$ and $Y_2$, or both $Y_1$ and $Y_3$, or both $Y_2$ and $Y_3$ in case of ribosyl; and $Y_1$, or both $Y_1$ and $Y_2$ or both $Y_2$ and $Y_3$ in case of arabinosyl, represent a phosphate, a pyrophosphate, a triphosphate, or a salt thereof, the balance of $Y_1$, $Y_2$ and $Y_3$ representing a hydroxyl group, wherein said salt is a pharmaceutically acceptable salt.

15. The nucleotide derivative as claimed in claim 1, wherein said derivative is an $N^4$-acyl-1-β-D-arabinofuranosylcytosine-3',5'-diphosphate or a sodium salt thereof.

16. The nucleotide derivative as claimed in claim 1, wherein said derivative is an $N^4$-acyl-1-β-D-arabinofuranosylcytosine-2',3'-diphosphate or a pharmaceutically acceptable salt thereof.

17. The nucleotide derivative as claimed in claim 1, wherein said derivative is an $N^4$-acyl-1-β-D-arabinofuranosylcytosine-2',3'-diphosphate or a sodium salt thereof.

18. The nucleotide derivative as claimed in claim 1, wherein said derivative is an $N^4$-acyl-1-β-D-arabinofurabosylcytosine-2'-phosphate or a pharmaceutically acceptable salt thereof.

19. The nucleotide derivative as claimed in claim 1, whrerin said derivative is an $N^4$-acyl-1-β-D-arabinofuranosylcytosine-2'-phosphate or a sodium salt thereof.

20. The nucleotide derivative as claimed in claim 1, whrerin said derivative is an $N^4$-acyl-1-β-D-arabinofuranosylcytosine-5'-pyrophosphate or a pharmaceutically acceptable salt thereof.

21. The nucleotide derivative as claimed in claim 1, wherein said derivative is an $N^4$-acyl-1-β-D-arabinofuranosylcytosine-5'-pyrophosphate or a sodium salt.

22. The nucleotide derivative as claimed in claim 1, wherein said derivative is an $N^4$-acyl-1-β-D-arabinofuranosylcytosine-5'-triphosphate or a pharmaceutically acceptable salt thereof.

23. The nucleotide derivative as claimed in claim 1, wherein said derivative is an $N^4$-acyl-1-β-D-arabinofuranosylcytosine-5'-triphosphate or a sodium salt thereof.

24. The nucleotide derivative as claimed in claim 1, wherein X is selected from the group consisting of a halogen atom, an alkyl group having 1 to 4 carbon atoms and a trifluoromethyl group.

25. The nucleotide derivative as claimed in claim 1, wherein one of $Y_1$ and $Y_3$ or both $Y_1$ and $Y_3$, or both $Y_2$ and $Y_3$ in case of ribosyl; and one of $Y_1$ and $Y_3$, or both $Y_1$ and $Y_2$ or both $Y_2$ and $Y_3$ in case of arabinosyl, represent a phosphate, a pyrophosphate, a triphosphate, or a salt thereof, the balance of $Y_1$, $Y_2$ and $Y_3$ representing a hydroxyl group, wherein said salt is a pharmaceutically acceptable salt.

* * * * *